US012102661B2

(12) United States Patent
Hou et al.

(10) Patent No.: US 12,102,661 B2

(45) Date of Patent: Oct. 1, 2024

(54) ACE INHIBITORY PEPTIDE COMPOSITION DERIVED FROM GINKGO PROTEIN AND PREPARATION METHOD AND APPLICATION THEREOF

(71) Applicant: NORTHEAST AGRICULTURAL UNIVERSITY, Heilongjiang (CN)

(72) Inventors: Juncai Hou, Harbin (CN); Zhanmei Jiang, Harbin (CN); Jiage Ma, Harbin (CN); Ruijie Shi, Yuncheng (CN); Jialun Hu, Chifeng (CN); Meng Li, Harbin (CN); Liya Gu, Harbin (CN)

(73) Assignee: NORTHEAST AGRICULTURAL UNIVERSITY, Harbin (CN)

( * ) Notice: Subject to any disclaimer, the term of this patent is extended or adjusted under 35 U.S.C. 154(b) by 0 days.

(21) Appl. No.: 18/157,081

(22) Filed: Jan. 20, 2023

(65) Prior Publication Data

US 2023/0142954 A1 May 11, 2023

Related U.S. Application Data

(62) Division of application No. 17/455,684, filed on Nov. 19, 2021, now abandoned.

(30) Foreign Application Priority Data

Nov. 23, 2020 (CN) ........................ 202011321061.X

(51) Int. Cl.
*A61K 38/16* (2006.01)
*A61K 38/08* (2019.01)
*A61K 38/10* (2006.01)

(52) U.S. Cl.
CPC ............ *A61K 38/168* (2013.01); *A61K 38/08* (2013.01); *A61K 38/10* (2013.01)

(58) Field of Classification Search
None
See application file for complete search history.

(56) References Cited

FOREIGN PATENT DOCUMENTS

| | | | | | |
|---|---|---|---|---|---|
| AU | 2019101528 | A4 | | 1/2020 | |
| AU | 2020103832 | A4 | * | 2/2021 | |
| CN | 102475884 | B | | 8/2013 | |
| CN | 103275179 | A | | 9/2013 | |
| CN | 104558110 | A | | 4/2015 | |
| CN | 104945502 | A | | 9/2015 | |
| CN | 106591405 | A | | 4/2017 | |
| CN | 104945469 | B | | 9/2018 | |
| CN | 105330721 | B | | 9/2018 | |
| CN | 110105430 | A | | 8/2019 | |
| CN | 110183516 | A | | 8/2019 | |
| CN | 110194786 | A | * | 9/2019 | C07K 7/06 |
| CN | 110372778 | A | | 10/2019 | |
| CN | 109206483 | B | | 7/2021 | |
| CN | 109293740 | B | | 7/2021 | |

OTHER PUBLICATIONS

First Office Action in Chinese Application No. 202011321061.X mailed on Aug. 13, 2021, 8 pages.
GenBank AAS79687.1, 2016, 2 pages.
GenBank BAL72618.1, 2012, 1 page.
CAS RN 158856-61-2, 1994, 1 page.
CAS RN 171042-05-0, 1995, 1 page.
CAS 171042-06-1, 1995, 1 page.

* cited by examiner

*Primary Examiner* — Sudhakar Katakam
*Assistant Examiner* — Zachary J Miknis

(57) ABSTRACT

The present disclosure provides ACE inhibitory peptide composition derived from ginkgo protein and preparation method and application thereof, belonging to the technical field of food and medicine. The ACE inhibitory peptide composition derived from ginkgo protein mainly consists of six small molecular peptides with amino acid sequences of GFDGR (SEQ ID NO. 1), NDPGR (SEQ ID NO. 2), LDQTYRP (SEQ ID NO. 3), REHETIIL (SEQ ID NO. 4), LRMPGPPSDDY (SEQ ID NO. 5) and LRMPGPPSD-DYER (SEQ ID NO. 6). The specific preparation process includes preparation of ginkgo protein, hydrolysis of ginkgo protein, enzymolysis and hydrolysis of ginkgo protein to obtain crude ACE inhibitory peptide, and separation and purification of ACE inhibitory peptide composition derived from ginkgo protein.

4 Claims, 14 Drawing Sheets

Specification includes a Sequence Listing.

ACE INHIBITORY PEPTIDE COMPOSITION DERIVED FROM GINKGO PROTEIN AND PREPARATION METHOD AND APPLICATION THEREOF

CROSS-REFERENCE TO RELATED APPLICATIONS

This application is a divisional application of U.S. patent application Ser. No. 17/455,684 filed on Nov. 19, 2021, which claims priority to Chinese Patent Application No. 202011321061.X, filed on Nov. 23, 2020, the contents of which are hereby incorporated by reference.

SEQUENCE LISTING

The instant application contains a Sequence Listing which has been submitted electronically in XML format and is hereby incorporated by reference in its entirety. The XML copy, created on Jan. 11, 2023, is named "20254-D001US01-sequence listing" and is 6,248 bytes in size.

TECHNICAL FIELD

The disclosure relates to the technical field of food and medicine, and in particular, to an ACE inhibitory peptide composition derived from ginkgo protein and a preparation method and application thereof.

BACKGROUND

Hypertension is a chronic disease that is extremely harmful to human health, and the main controllable risk factor for cardiovascular and cerebrovascular diseases such as coronary heart disease and stroke. The result of research shows that a 5 mmHg decrease in blood pressure is equivalent to reducing the risk rate of cardiovascular and cerebrovascular diseases by 16%. At present, the first-line drugs for treating hypertension mainly include diuretics, receptor blockers, angiotensin converting enzyme inhibitors, calcium channel blockers, receptor blockers and angiotensin receptor antagonists. Every year, hundreds of billions of dollars are spent on antihypertensive drugs all over the world. Meanwhile, when these drugs are used to control hypertension, there may be various side effects, including hypotension, increased blood potassium level, decreased renal function, cough, angioedema, rash and fetal malformation, etc. Because of the side effects of medication, antihypertensive functional factors from safe and natural food are important for non-medication treatment of hypertension in the future.

Ginkgo protein not only has nutritional function, but also has important physiological function, which is a good source of bioactive peptides. Therefore, it is necessary to study the antihypertensive peptides derived from ginkgo protein (for example, ACE inhibitory peptides) and their preparation methods (for example, applying biological enzyme technology), and develop products of antihypertensive peptides derived from ginkgo protein (for example, ACE inhibitory peptides) with independent intellectual property rights in China, which is of important academic significance and practical application value.

SUMMARY

To solve the problems in the prior art, the present disclosure provides an ACE inhibitory peptide composition derived from ginkgo protein, a preparation method and application thereof, so as to use natural and safe foods instead of medicines to treat hypertension, avoid various side effects emerging in medication for treating hypertension, establish the technological process and parameters using enzyme technology to prepare ACE inhibitory peptide composition derived from ginkgo protein, and to provide theoretical basis and technical support for industrial production.

To achieve the above purpose, the present disclosure provides the following solution.

The present disclosure provides an ACE inhibitory peptide composition derived from ginkgo protein, which mainly consists of six small molecular peptides with amino acid sequences of GFDGR (SEQ ID NO. 1), NDPGR (SEQ ID NO. 2), LDQTYRP (SEQ ID NO. 3), REHETIIL (SEQ ID NO. 4), LRMPGPPSDDY (SEQ ID NO. 5) and LRMPGPPSDDYER (SEQ ID NO. 6).

The disclosure provides a preparation method of the ACE inhibitory peptide composition derived from ginkgo protein, which specifically includes the following steps:

(1) Preparation of Defatted Ginkgo Nut Powder
- defatting ginkgo nut powder with petroleum ether to obtain defatted ginkgo nut powder;

(2) Preparation of Ginkgo Protein
- firstly, after mixing the defatted ginkgo nut powder obtained in step (1) with water, adding NaOH solution to adjust its pH to 10.0,
- then, extracting at 40-45° C.,
- ansubsequently, after centrifugation the extract to obtain supernatant, adjusting pH of the supernatant to 4-4.5 with HCl solution, and centrifuging the supernatant after pH adjustment to obtain ginkgo protein powder;

(3) Hydrolysis of Ginkgo Protein
- firstly, preparing the ginkgo protein powder obtained in step (2) into a protein solution,
- then, adding NaOH solution into the protein solution to adjust the pH value,
- and then adding enzyme to hydrolyze the protein solution; and
  - centrifuging after hydrolysis and collecting supernatant to obtain ginkgo protein hydrolysate;

(4) Ultrafiltration Separation of Ginkgo Protein Hydrolysate
- ultrafiltering and separating the ginkgo protein hydrolysate obtained in step (3) to obtain ultrafiltration permeate;

(5) Preparation of Crude ACE Inhibitory Peptide Derived from Ginkgo Protein
- freeze-drying the ultrafiltration permeate obtained in step (4) to obtain crude ACE inhibitory peptide derived from ginkgo protein;

(6) Preparation of ACE Inhibitory Peptide Composition Derived from Ginkgo Protein
- separating the crude ACE inhibitory peptide derived from ginkgo protein obtained in step (5) by two-step reversed-phase chromatography,
- then, purifying by high performance liquid chromatography to obtain the ACE inhibitory peptide composition derived from ginkgo protein.

Further, the mass-volume ratio of ginkgo nut powder and petroleum ether in step (1) is 1:12.

Further, the concentration of NaOH solution in step (2) is 6 mol/L, and the concentration of HCl solution is 6 mol/L.

Further, the centrifugation condition is 4000 r/min for 30 min.

Further, the enzyme used in the hydrolysis process in step (3) is AS1.398 neutral protease.

Further, the concentration of the protein solution in step (3) is 7.17%.

Furthermore, the hydrolysis conditions in step (3) are that the temperature is 45.61° C., the mass ratio of enzyme to substrate is 5%, and the time is 6 h.

Further, the ultrafiltration mode in step (4) is ultrafiltration through an ultrafiltration membrane with a molecular weight cut-off of 3 kDa.

The disclosure also provides an application of the ACE inhibitory peptide composition derived from ginkgo protein in preparing medicine for preventing and treating hypertension.

The present disclosure discloses the following technical effects.

The ACE inhibitory peptide composition derived from ginkgo protein is of very important research value and practical value in preventing and treating hypertension because of its high safety and no side effects.

In the present disclosure, the hydrolysis process of ACE inhibitory peptide composition derived from ginkgo protein is optimized, and ACE inhibitory activities of ginkgo protein hydrolysates from four proteases (for example, AS1.398 neutral protease hydrolysate, trypsin hydrolysate, papain hydrolysate and Alcalase hydrolysate) are compared and analyzed. The results show that four protease hydrolysates have different ACE inhibitory activities, among which AS1.398 neutral protease hydrolysate has the highest ACE inhibitory activity. Therefore, it can be seen from this research result that the type of protease is the key factor to obtain strong ACE inhibitory peptide.

According to the present disclosure, in the process of optimizing hydrolysis conditions, the ACE inhibitory activity is taken as the detection index, and the response surface design of three factors and three levels is used to optimize the optimum preparation conditions of ACE inhibitory peptide composition, which are as follows: extraction temperature is 45.61° C., pH is 7.38, substrate concentration is 7.17%, and ACE inhibitory rate is 90.52%.

In the present disclosure, ultrafiltration technology and reversed-phase chromatography technology are employed to separate and purify ACE inhibitory peptide composition, and then two-dimensional mass spectrometry technology is adopted to identify the amino acid sequence composition of the peptide. The ACE inhibitory peptide composition derived from ginkgo protein can be effectively separated and extracted by using ultrafiltration technology. The ultrafiltrate obtained by 3 kDa ultrafiltration membrane has the strongest ACE inhibitory activity, which indicates that the ACE inhibitory activity derived from ginkgo protein hydrolysate mainly comes from short peptides with molecular weight less than 3 kDa. Source TM 5RPC ST 4.6/150 reversed-phase chromatographic column is used for fine separation and purification of functional components of ACE inhibitory peptide. The effect of one-step reversed-phase chromatography is good, but the purity of the separated components may not be high because the properties of ACE inhibitory peptide components are similar and have little difference. Therefore, after two-step reversed-phase chromatography and separation and purification by Advance Bio peptide column, the purity of the active components obtained is relatively high.

In the present disclosure, amino acid sequence analysis is carried out after separation and purification, and the amino acid sequences of six main active peptides in ACE inhibitory peptide composition derived from ginkgo protein is identified. A 4700 tandem time-of-flight mass spectrometer is used for mass spectrometry, and the amino acid sequences of the six main active peptides are determined to be GFDGR (SEQ ID NO. 1), NDPGR (SEQ ID NO. 2), LDQTYRP (SEQ ID NO. 3), REHETIIL (SEQ ID NO. 4), LRMPGPPSDDY (SEQ ID NO. 5) and LRMPGPPSDDYER (SEQ ID NO. 6).

DETAILED DESCRIPTION

Figure 1:
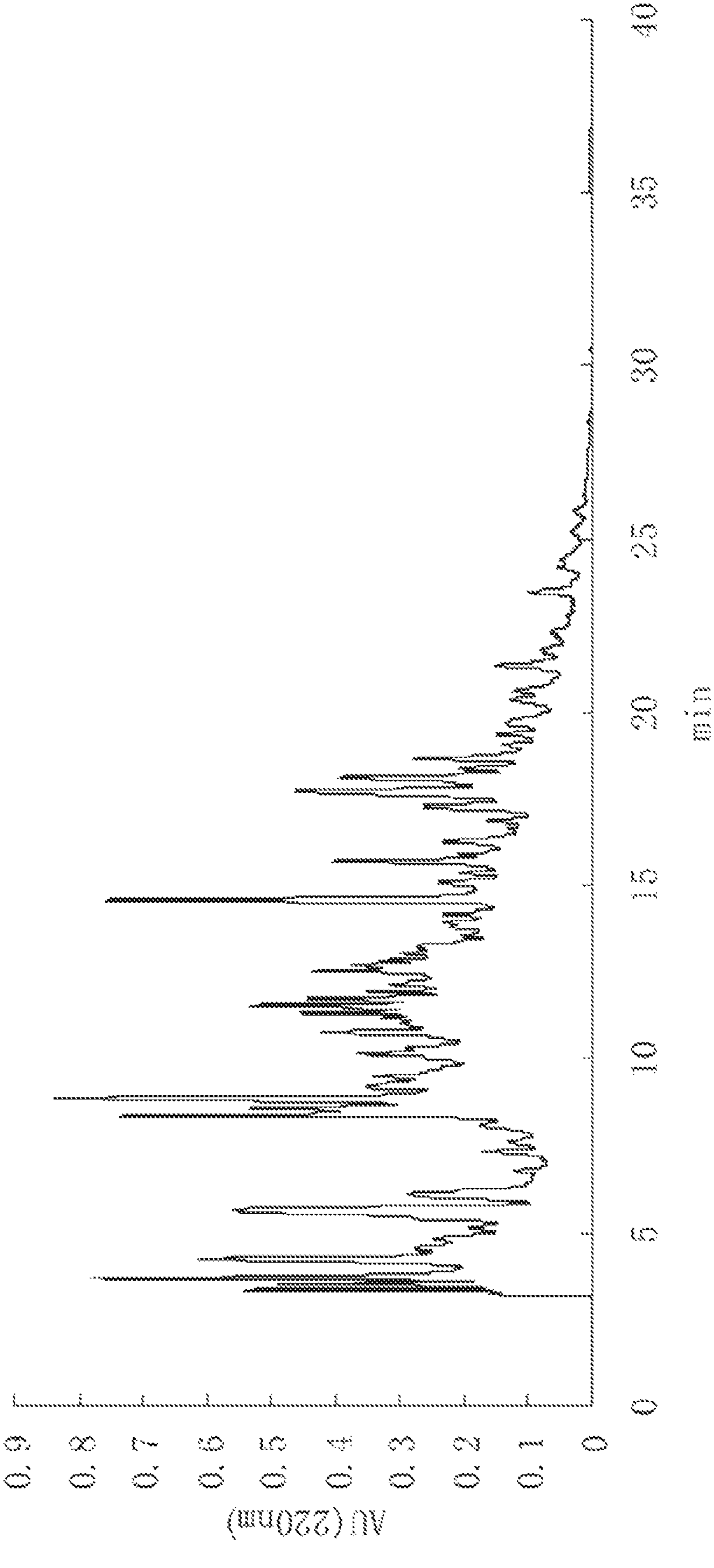
FIG. 1 is a chromatogram of crude ACE inhibitory peptide derived from ginkgo protein separated by SinoChrom ODS-BP C18 column according to some embodiments of the present disclosure.

The embodiments of the present disclosure will be further explained with reference to the accompanying figures. This detailed description should not be regarded as a limitation of the present disclosure, but should be understood as a more detailed description of certain aspects, characteristics and embodiments of the present disclosure.

It should be understood that the terms described in the present disclosure are only for describing specific embodiments, and are not intended to limit the present disclosure. In addition, for the numerical range in the present disclosure, it should be understood that every intermediate value between the upper limit and the lower limit of the range is also specifically disclosed. Intermediate values within any stated value or stated range and every smaller range between any other stated value or intermediate values within the stated range are also included in the present disclosure. The upper limit and lower limit of these smaller ranges can be independently included or excluded from the range.

Unless otherwise stated, all technical and scientific terms used herein have the same meanings as commonly understood by those skilled in the art described in the present disclosure. Although only preferred methods and materials are described in the present disclosure, any methods and materials similar or equivalent to those described herein may be used in the practice or testing of the present disclosure. All documents mentioned in this specification are incorporated by reference to disclose and describe methods and/or materials related to the documents. In case of conflict with any incorporated documents, the contents of this specification shall prevail.

Without departing from the scope or spirit of the present disclosure, it is obvious to those skilled in the art that many modifications and changes can be made to the specific embodiments of the present disclosure. Other embodiments derived from the description of the present disclosure will be apparent to the skilled person. The specification and embodiments of the present disclosure are only exemplary.

As used herein, "include", "comprise", "have", "contain", etc. are all open terms, which means including but not limited to.

Angioensin Converting Enzyme (ACE), also known as kininase II or peptidyl-carboxypeptidase, may catalyze the hydrolysis of angiotensin I to angiotensin II, which will further shrink blood vessels and increase blood pressure. ACE inhibitory peptide is a kind of antihypertensive peptide, which can block the production of angiotensin II with blood pressure-raising activity and promote the production of soothing peptide and enkephalin with blood pressure-lowering activity by combining with ACE competitively, thus playing a role in lowering blood pressure. ACE inhibitory peptides may be derived from different raw materials, such as ginkgo. Ginkgo protein has high nutritional function and important physiological function. ACE inhibitory peptide that is derived from ginkgo protein (also known as ACE inhibitory peptide derived from ginkgo protein) has the advantages of being natural, and safe without side effects, and is of very important research value and practical value in preventing and treating hypertension.

According to an aspect of the present disclosure, an ACE inhibitory peptide composition derived from ginkgo protein is provided. The ACE inhibitory peptide composition derived from ginkgo protein mainly consists of six small molecular peptides with amino acid sequences of GFDGR (SEQ ID NO. 1), NDPGR (SEQ ID NO. 2), LDQTYRP (SEQ ID NO. 3), REHETIIL (SEQ ID NO. 4), LRMPGPPSDDY (SEQ ID NO. 5) and LRMPGPPSDDYER (SEQ ID NO. 6). In some embodiments, the ACE inhibitory peptide composition derived from ginkgo protein is prepared from ginkgo protein, and the main preparation processes include preparation of ginkgo protein, hydrolysis of ginkgo protein, enzymatic hydrolysis of ginkgo protein to obtain crude ACE inhibitory peptide, and separation and purification of ACE inhibitory peptide composition derived from ginkgo protein. The prepared ACE inhibitory peptide composition derived from ginkgo protein has high ACE inhibitory activity (for example, the ACE inhibitory rate is over 90%), and has the advantages of being natural, safe and free of side effects, which can be effectively applied to the prevention and treatment of hypertension.

According to another aspect of the present disclosure, a preparation method of the ACE inhibitory peptide composition derived from ginkgo protein is provided.

In some embodiments, the method of preparing ACE inhibitory peptide composition derived from ginkgo protein may include the following steps. For more detailed steps of the method for preparing the ACE inhibitory peptide composition derived from ginkgo protein, please refer to Embodiment 1 later.

(1) Preparation of Defatted Ginkgo Nut Powder

In some embodiments, petroleum ether can be used to defat ginkgo nut powder to prepare degreased ginkgo nut powder. In some embodiments, the mass-volume ratios of ginkgo nut powder to petroleum ether may include 1:11, 1:12, 1:13, 1:14, etc.

(2) Preparation of Ginkgo Protein

In some embodiments, the defatted ginkgo nut powder obtained in the above step may be mixed with water to obtain an aqueous solution of defatted ginkgo nut powder. Thereafter, NaOH can be used to adjust the pH value of the aqueous solution of defatted ginkgo nut powder. In some embodiments, the concentration of the NaOH solution may be any concentration. In some embodiments, the concentration of the NaOH solution may be 6 mol/l.

In some embodiments, the pH value may be between 9.0 and 11.0. For example, the pH value of defatted ginkgo nut powder aqueous solution may include 9.0, 9.2, 9.4, 9.6, 9.8, 10.0, 10.2, 10.4, 10.6, 10.8 or 11.0. In some embodiments, the pH may be 10.0.

After adjusting the pH, the aqueous solution of defatted ginkgo nut powder may be extracted at 40-50° C. to obtain an extract. In some embodiments, the aqueous solution of defatted ginkgo nut powder may be extracted at 40-45° C.

Then the extract may be centrifuged to obtain the supernatant, and then the pH is adjusted to 4-4.5 with HCl; and the extract is centrifuged again to obtain the supernatant, i.e. the ginkgo protein powder. In some embodiments, the concentration of the HCl solution may be any concentration. In some embodiments, the concentration of the HCl solution may be 6 mol/l.

(3) Hydrolysis of Ginkgo Protein

In some embodiments, ginkgo protein powder may be formulated as a protein solution with a certain substrate concentration. The substrate concentration here refers to the mass concentration of ginkgo protein powder in a solvent (for example, water). In some embodiments, the substrate concentration may be any value between 6.5% and 7.5%. For example, the substrate concentration may be 6.5%, 6.6%, 6.7%, 6.8%, 6.9%, 7.0%, 7.1%, 7.17%, 7.2%, 7.3%, 7.4% or 7.5%. In some embodiments, the substrate concentration may be 7.17%. In some embodiments, the substrate concentration may be 7%. For the selection of substrate concentration, please refer to Test Example 2.

Next, NaOH solution is added to the protein solution to adjust the pH value. In some embodiments, the adjusted pH ranges from 6.5 to 8.5. For example, the pH value of protein solution may be 6.5, 6.8, 7.0, 7.1, 7.2, 7.3, 7.35, 7.38, 7.4, 7.5, 7.6, 7.7, 7.8, 8.0, 8.3 or 8.4. In some embodiments, the pH of the protein solution is 7.40. In some embodiments, the pH value of the protein solution is 7.38. In some embodiments, the pH value of the protein solution is 7. For the selection of pH value, please refer to Test Example 2.

When the temperature of the reaction system (or the reaction) reaches a certain temperature value, protease with a certain mass concentration ratio with the substrate is added for hydrolysis. In some embodiments, the temperature value may be any one of 40° C.-50° C. For example, the temperature value may be 40° C., 41° C., 42° C., 43° C., 44° C., 45° C., 45.6° C., 45.61° C., 46° C., 47° C., 48° C., 49° C. or 50° C. In some embodiments, the temperature value may be 45.6° C. In some embodiments, the temperature value may be 45.61° C. For the selection of extraction temperature, please refer to Test Example 2.

In some embodiments, the protease may include enzymes capable of hydrolyzing proteins, including but not limited to AS1.398 neutral protease, papain, Alcalase, trypsin, etc. In some embodiments, the protease is AS1.398 neutral protease. In some embodiments, the protease is Alcalas. In some embodiments, the protease is papain. For the selection of protease, please refer to Test Example 1.

In some embodiments, the mass concentration ratio of protease to substrate is any value between 4% and 7%. In some embodiments, the mass concentration ratio of protease to substrate is 5%.

After hydrolysis for a period of time, the supernatant is centrifuged and collected to obtain ginkgo protein hydrolysate. The hydrolysis period of time of protein solution may be between 5 h and 14 h. For example, in some embodiments, the hydrolysis period of time of the protein solution may be 5 h, 6 h, 7 h, 8 h, 9 h, 10 h, 11 h, 12 h or 14 h. In some embodiments, the hydrolysis time period of the protein solution may be 6 h. For the selection of hydrolysis time periods, please refer to Test Example 3.

In some embodiments, ginkgo protein hydrolysate may be obtained by centrifugation and collecting supernatant. In some embodiments, the centrifugation condition may be 4000 r/min, and the centrifugation time may be 30 min.

(4) Ultrafiltration Separation of Ginkgo Protein Hydrolysate

In some embodiments, ginkgo protein hydrolysate may be separated by an ultrafiltration device to prepare ultrafiltration permeate. In some embodiments, the ultrafiltration device may include, but is not limited to, filtering bags, ultrafiltration tubes, ultrafiltration membranes, etc. In some embodiments, the molecular weight cut-off of the ultrafiltration device may be below 10 kDa. For example, the molecular weight cut-off of ultrafiltration devices may be 9 kDa, 8 kDa, 7 kDa, 6 kDa, 5 kDa, 4 kDa, 3 kDa, 2 kDa or 1 kDa. In some embodiments, the molecular weight cut-off of the ultrafiltration device may be 3 kDa. For the selection of molecular weight cut-off, please refer to Test Example 4.

(5) Preparation of Crude ACE Inhibitory Peptide Derived from Ginkgo Protein

In some embodiments, the ultrafiltration permeate may be freeze-dried to obtain crude ACE inhibitory peptide derived from ginkgo protein.

(6) Preparation of ACE Inhibitory Peptide Composition Derived from Ginkgo Protein In some examples, crude ACE inhibitory peptide derived from ginkgo protein may be separated by SinoChrom ODS-BP C18 reversed-phase chromatographic column, and a first component with the strongest ACE inhibitory activity is collected. Particularly, the crude ACE inhibitory peptide of ginkgo protein is eluted and separated at the wavelength of 220 nm of SinoChrom ODS-BP C18 reversed-phase chromatographic column, and the first component with the strongest ACE inhibitory activity is collected.

In some embodiments, the first component with the strongest ACE inhibitory activity may be further separated at the wavelength of 220 nm by using an Advance Bio peptide chromatographic column, and a second component with the strongest ACE inhibitory activity from the first component may be collected and determined.

In some embodiments, purification and purity identification may be performed on the crude ACE inhibitory peptide of ginkgo protein by Advance Bio peptide chromatographic column to prepare ACE inhibitory peptide composition derived from ginkgo protein.

According to yet another aspect of the present disclosure, a use of ACE inhibitory peptide composition derived from ginkgo protein in preparing medicines for preventing and treating hypertension is provided. As the main active ingredient of hypertension medicine, the ACE inhibitory peptide composition derived from ginkgo protein prepared in the present disclosure can effectively reduce hypertension. The ACE inhibitory peptide composition derived from ginkgo protein may be made into medicine for preventing and treating hypertension together with other auxiliary materials to treat hypertension.

The ACE inhibitory peptide composition derived from ginkgo protein, preparation method and application thereof provided in the present disclosure may bring beneficial effects including but not limited to: (1) the preparation process of the ACE inhibitory peptide composition derived from ginkgo protein is simple, the production cost is low, the reaction conditions are mild, and the product is safe without toxic and side effects, which can be used to develop drugs or health products for preventing and treating diabetes and hypertension; (2) the conventionally ginkgo nuts are mainly consumed as vegetables and snacks; at present, the ginkgo products on market are mainly ginkgo nut powder or ginkgo tea, hence limiting the use; therefore, using ginkgo protein as raw materials to prepare ACE inhibitory peptide enriches the edible and medicinal properties of ginkgo products; (3) ACE inhibitory peptide composition derived from ginkgo protein prepared by using AS1.398 neutral protease has the advantages of high ACE inhibitory activity, good safety and no side effects.

Embodiments

The experimental methods in the following examples are all conventional methods unless otherwise specified. The test materials used in the following examples, unless otherwise specified, are purchased from conventional biochemical reagent companies. For the quantitative tests in the following examples, three repeated experiments are set, and the results are averaged.

Embodiment 1 Preparation of ACE Inhibitory Peptide Composition Derived from Ginkgo Protein 1. Preparing Defatted Ginkgo Nut Powder In some embodiments, defatted ginkgo nut powder may be prepared as follows.

The *Ginkgo biloba* is peeled and membranous inner seed coat is removed, and then the *Ginkgo biloba* is put into a freeze dryer for freeze-drying for 24-48 h; the dried *Ginkgo biloba* is grinded in a high-speed grinder and is sieved to obtain ginkgo nut powder.

The ginkgo nut powder is mixed with petroleum ether in a ratio of 1:12 (by mass and volume); then the mixture is placed at 0-4° C. and stirred once every 1-2 h; the petroleum ether is changed after 4-6 h, and this operation is repeated for 3-4 times until ginkgo nut powder is white.

Then, the ginkgo nut powder is separated from the petroleum ether, and the wet ginkgo nut powder is collected.

Finally, at room temperature, the wet ginkgo nut powder is placed in a ventilation system until petroleum ether is completely volatilized, thus obtaining defatted ginkgo nut powder.

2. Preparation of Ginkgo Protein

In some embodiments, ginkgo protein may be prepared as follows.

The defatted ginkgo nut powder is dissolved in distilled water to prepare a solution with a ratio of material to liquid of 1:18, and 6 mol/L of NaOH solution is added to adjust its pH to 10.0. Heat preservation and extraction is carried out at 40-45° C. for 1 h, then centrifugating is carried out at 4000 r/min for 30 min to collect supernatant. Then, the pH is adjusted to 4-4.5 with 6 mol/L HCl, the supernatant is rested for 2 h and centrifuged at 4000 r/min for 30 min; the precipitate is collected in a freeze dryer for vacuum drying to obtain ginkgo protein powder.

3. Hydrolysis of Ginkgo Protein.

In some embodiments, ginkgo protein may be hydrolyzed as follows.

A certain amount of ginkgo protein powder is accurately weighed to prepare a protein solution with a substrate concentration of 7.17%; 4 mol/L of NaOH solution is added to adjust the pH value to 7.40, and then the mixture is put in a constant temperature water bath. When the temperature of the reaction system (or the reaction) reaches 45.6° C., As1.398 neutral protease with a mass concentration ratio of enzyme to substrate of 5% is added for hydrolysis. In the whole hydrolysis process, 1 mol/L of NaOH is added while stirring to maintain a constant pH value. After hydrolysis for 6 h, the reaction system is kept in boiling water bath for 15-20 min to stop the reaction. The hydrolysate is centrifuged at 4000 r/min for 30 min, and the supernatant is collected to obtain ginkgo protein hydrolysate.

For the selection of hydrolysis conditions in this step, please refer to Test Examples 1-3 below.

4. Ultrafiltration Separation of Ginkgo Protein Hydrolysate

In some embodiments, ginkgo protein hydrolysate may be separated by ultrafiltration as follows.

Ginkgo protein hydrolysate is separated by ultrafiltration membrane with molecular weight cut-off of 3 kDa, and then ultrafiltration permeate is collected and obtained.

For the selection of molecular weight cut-off in this step, please refer to the content of Test Example 4 below.

5. Preparation of Crude ACE Inhibitory Peptide Derived from Ginkgo Protein

In some embodiments, crude ACE inhibitory peptide derived from ginkgo protein may be prepared as follows.

The ultrafiltration permeate obtained in step 4 is freeze-dried to obtain crude ACE inhibitory peptide derived from ginkgo protein.

6. Preparation of ACE Inhibitory Peptide Composition Derived from Ginkgo Protein In some embodiments, the ACE inhibitory peptide composition derived from ginkgo protein may be prepared as follows.

(1) Separation of Crude ACE Inhibitory Peptide Derived from Ginkgo Protein by Two-Step Reversed-Phase Chromatography.

① The First-Step Reversed-Phase Chromatographic Separation

The crude ACE inhibitory peptide derived from ginkgo protein prepared by enzymatic method has complex components, and only the components with strong ACE inhibitory activity may be obtained after ultrafiltration separation by ultrafiltration membrane with molecular weight cut-off of 3 KDa. By high performance liquid chromatography analysis, the purity of the components is low, which is not a single component, so the next chromatographic separation must be carried out. In the present disclosure, SinoChrom ODS-BP C18 reversed-phase chromatographic column is selected to further separate and purify the highly active components obtained after ultrafiltration separation, and the components are eluted and separated at the wave length of 220 nm. The test results of reversed-phase chromatographic separation are shown in FIG. 1.

Figure 2:
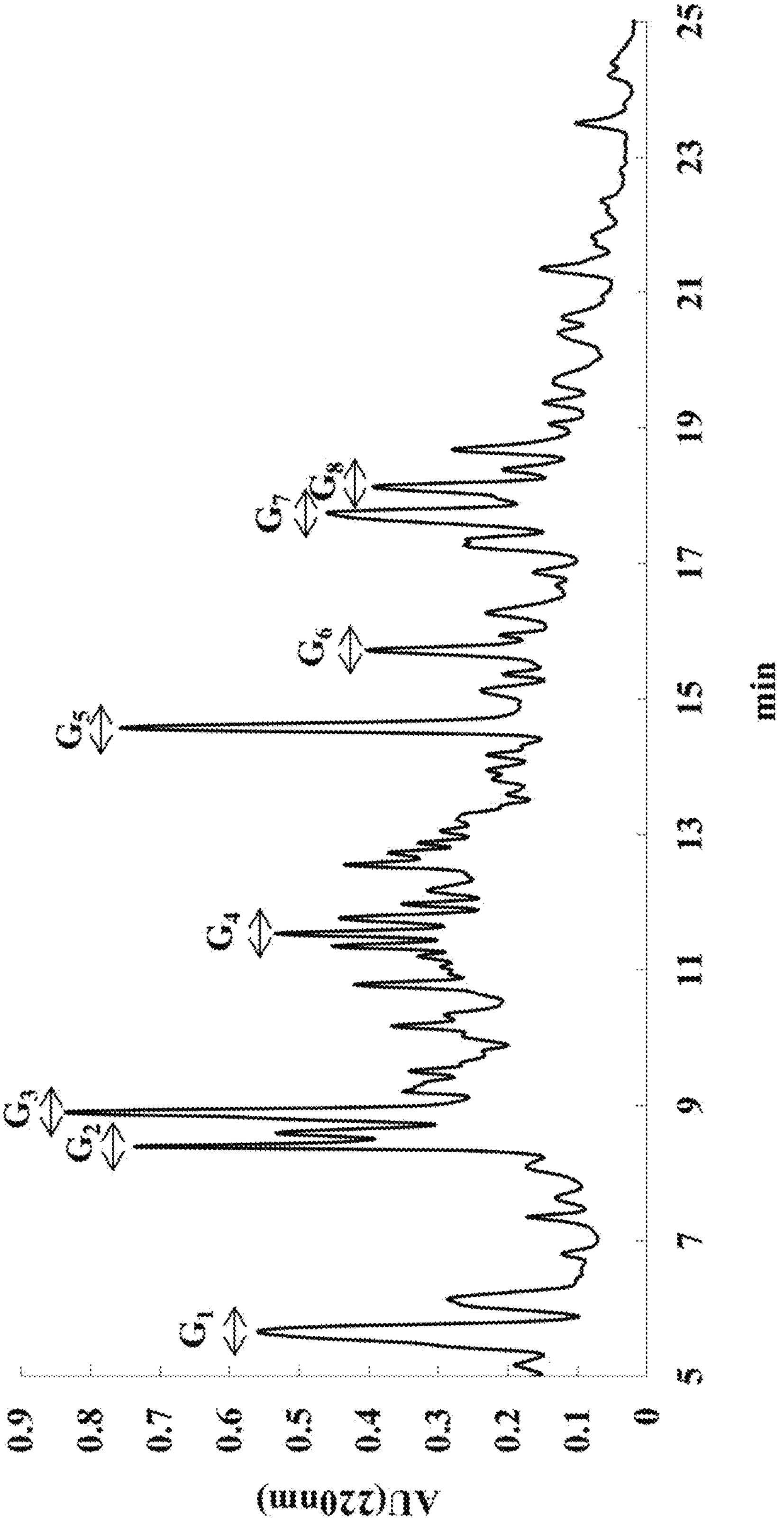
FIG. 2 is an enlarged view of the chromatogram of FIG. 1 according to some embodiments of the present disclosure.

Owing to the high resolution and good selectivity of SinoChrom ODS-BP C18 reversed-phase chromatographic column, several absorption peaks with different sizes still appear after elution and separation of the sample components, with sharp and symmetrical peaks and good separation effect. FIG. 1 is further enlarged into FIG. 2, and the chromatographic peaks in FIG. 2 are sequentially labeled as components G1, G2, G3, G4, G5, G6, G7 and G8, and then the eluent is collected according to the labeled chromatographic peaks. The determination result of ACE inhibitory activity derived from ginkgo protein of each collecting tube component is shown as FIG. 3. Duncan multiple comparative analysis is carried out on the data in FIG. 3, in which a, b, c and d represent different difference levels, data with the same letters are regarded as insignificant difference ($P<0.05$), and data without the same letters are regarded as significant difference ($P>0.05$).

Figure 3:
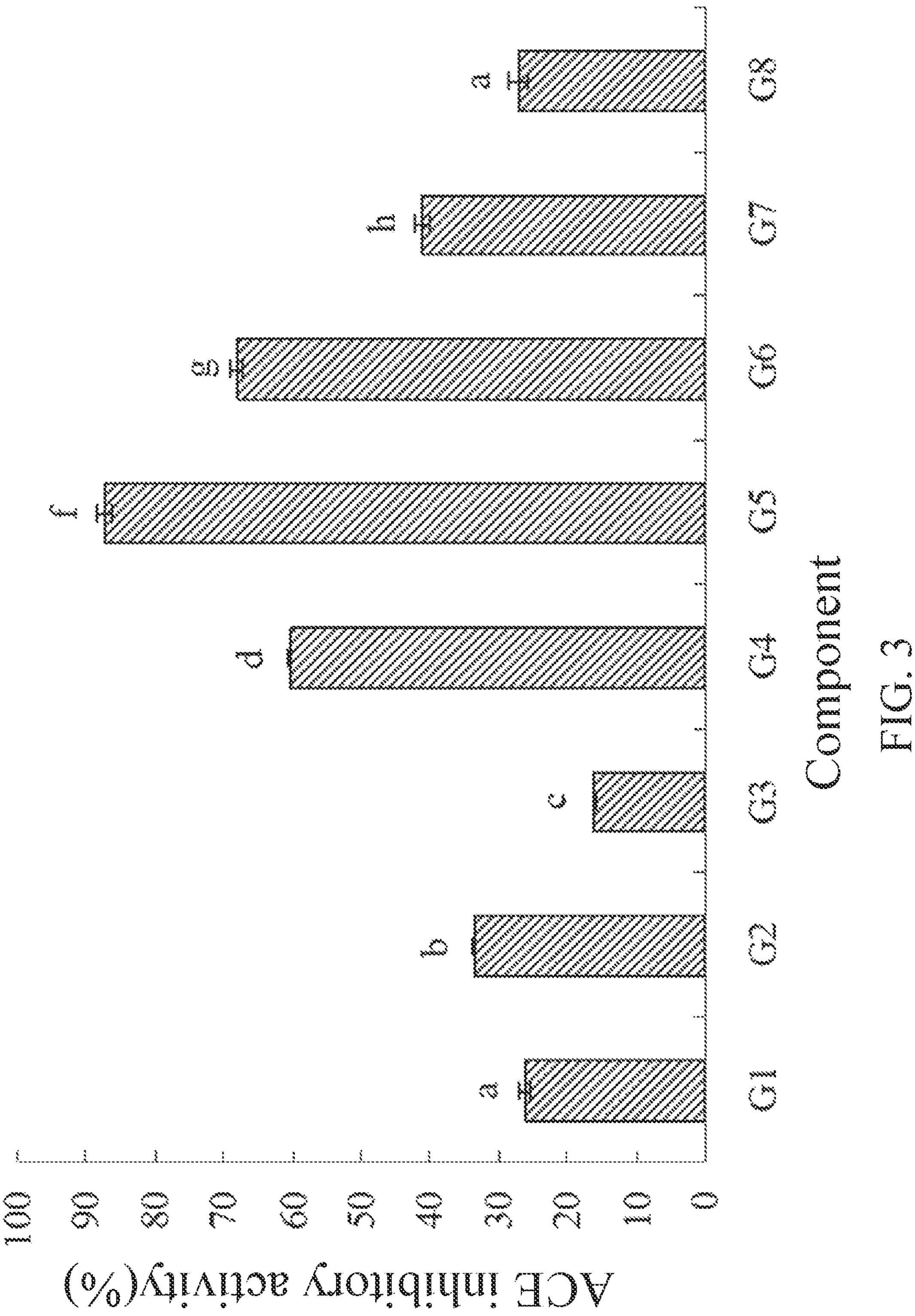
FIG. 3 illustrates a determination result of ACE inhibitory activities derived from ginkgo protein of components G1-G8 in FIG. 2 according to some embodiments of the present disclosure.

The determination results of ACE inhibitory activity derived from ginkgo protein in FIG. 3 show that different eluents show different ACE inhibitory activities, and the ACE inhibitory activity derived from ginkgo protein in component G5 (i.e., the component with the strongest ACE inhibitory activity, also referred to as the first component) is the strongest, so component G5 is selected as the further separation and purification component. Repeat the above samples several times and collect component G5, and continue to separate and purify after rotary evaporation and concentration.

② The Second-Step Reversed-Phase Chromatographic Separation

Component G5 with strong ACE inhibitory activity derived from ginkgo protein is obtained by one-step reversed-phase chromatographic separation, and the second-step reversed-phase chromatographic separation is carried out by using the high performance liquid chromatography system and the Advance Bio peptide column. The elution separation chromatogram of component G5 at the wavelength of 220 nm is shown as FIG. 4.

Figure 4:
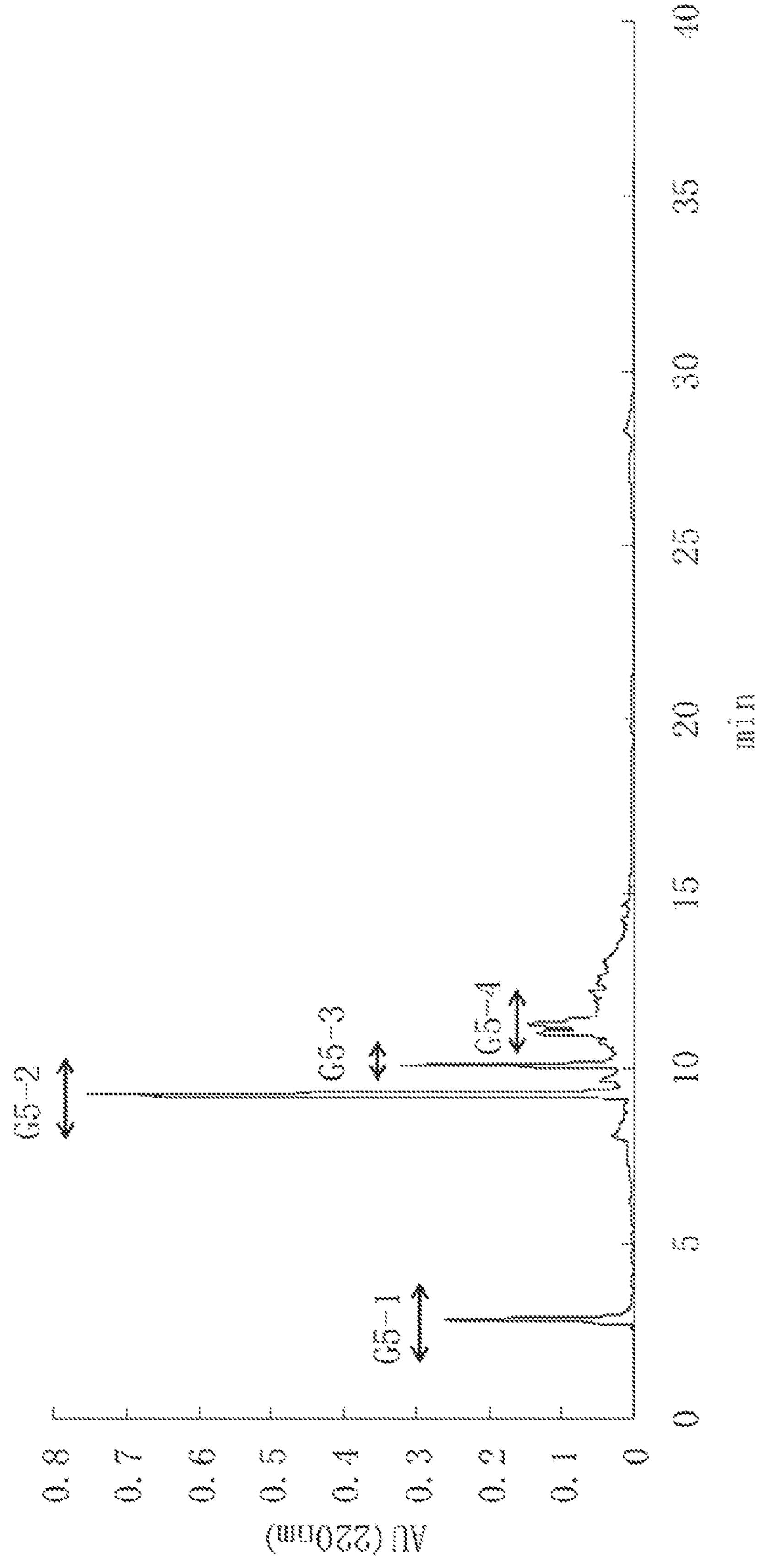
FIG. 4 is a chromatogram of component G5 separated by an Advance Bio peptide chromatographic column according to some embodiments of the present disclosure.

It can be seen from the separation results of reversed-phase chromatography in FIG. 4 that four main absorption peaks may be obtained after the separation of component G5 by reversed-phase chromatography, namely component G5-1, component G5-2, component G5-3 and component G5-4. According to the absorption peak, separate collection is carried out, and the ACE inhibitory activity derived from ginkgo protein of each collection tube component is determined. The test results are shown in FIG. 5.

Figure 5:
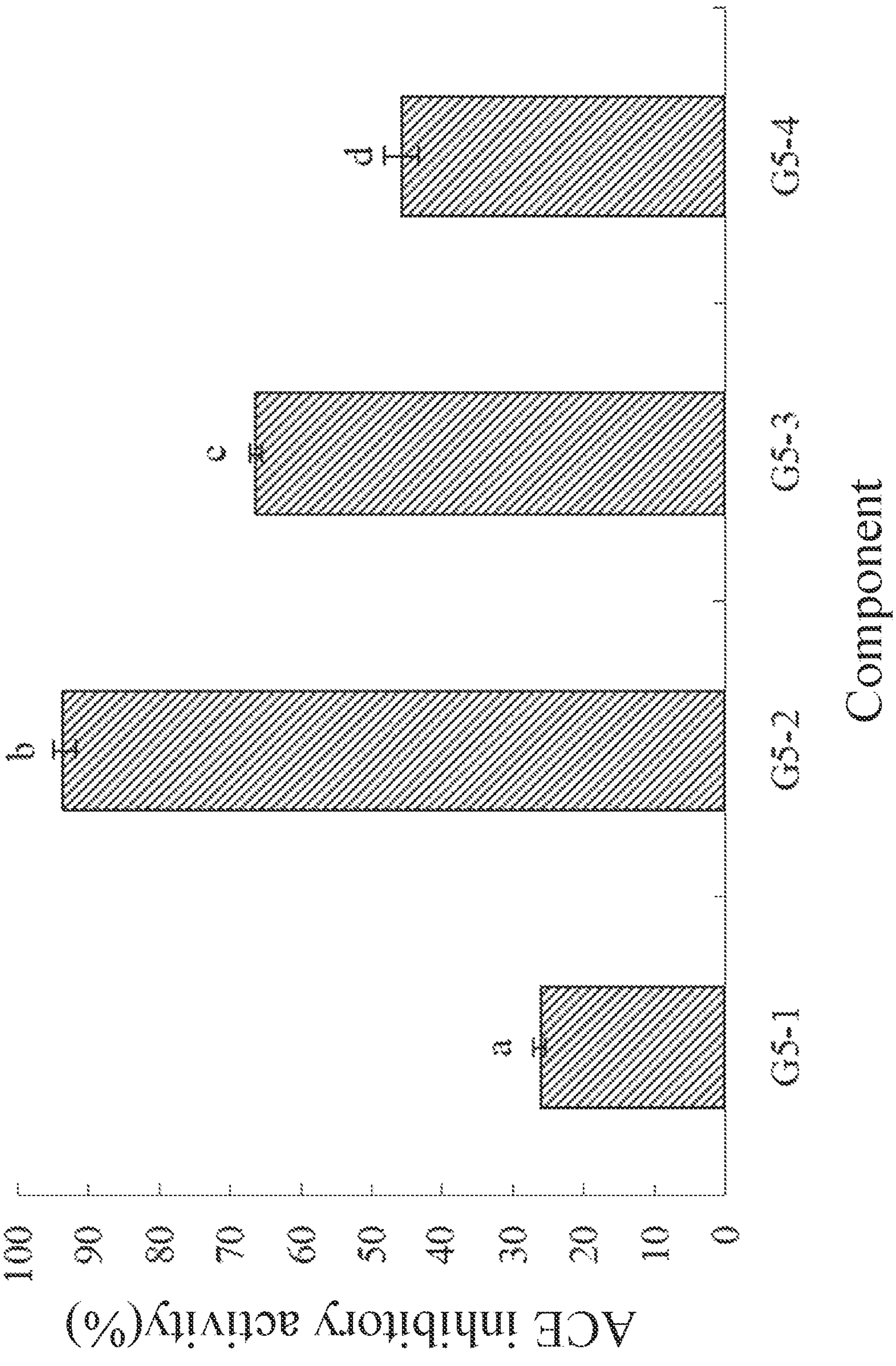
FIG. 5 is a graph showing the determination result of ACE inhibitory activities derived from ginkgo protein of components G5-1, G5-2, G5-3 and G5-4 in FIG. 4 according to some embodiments of the present disclosure.

It can be seen from the analysis results in FIG. 5 that the ACE inhibitory activity of the maximum absorption peak of component G5-2 (i.e., the component with the strongest ACE inhibitory activity of component G5, also referred to as the second component) is the strongest. Repeat the above samples several times and collect G5-2 with relatively high purity. Duncan multiple comparative analysis is carried out on the data in FIG. 5, in which a, b, c and d represent different difference levels, data with the same letters are regarded as insignificant difference ($P<0.05$), and data without the same letters are regarded as significant difference ($P>0.05$).

(2) Purification, Purity Identification and Structural Sequence Analysis of ACE Inhibitory Peptide Composition ① The purity of G5-2 is identified by high performance liquid chromatography (HPLC) with Advance Bio peptide column. Chromatographic separation diagram after purity identification is shown in FIG. 6.

Figure 6:
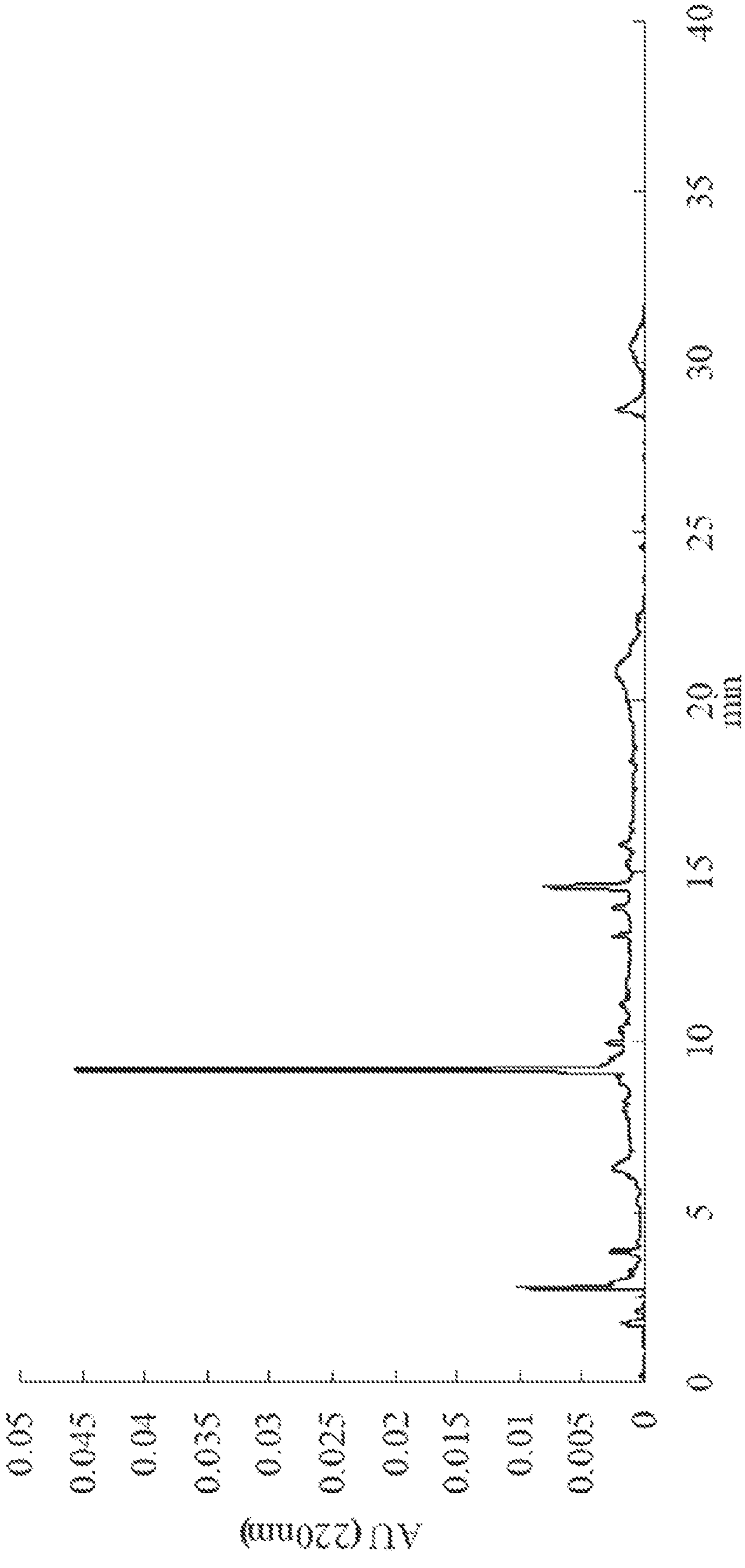
FIG. 6 is a chromatogram of component G5 separated by an Advance Bio peptide chromatographic column according to some embodiments of the present disclosure.

From the analysis of the test results in FIG. 6, it can be seen that the component G5-2 contains only one strong absorption peak, while the other peaks are less and the purity is higher. The component G5-2 is the ACE inhibitory peptide composition derived from ginkgo protein.

Embodiment 2 Sequence Analysis of ACE Inhibitory Peptide Composition Derived from Ginkgo Protein In some embodiments, sequence analysis of ACE inhibitory peptide composition derived from ginkgo protein can be performed using mass spectrometry.

A. Primary Mass Spectrometry Analysis

Figure 7:
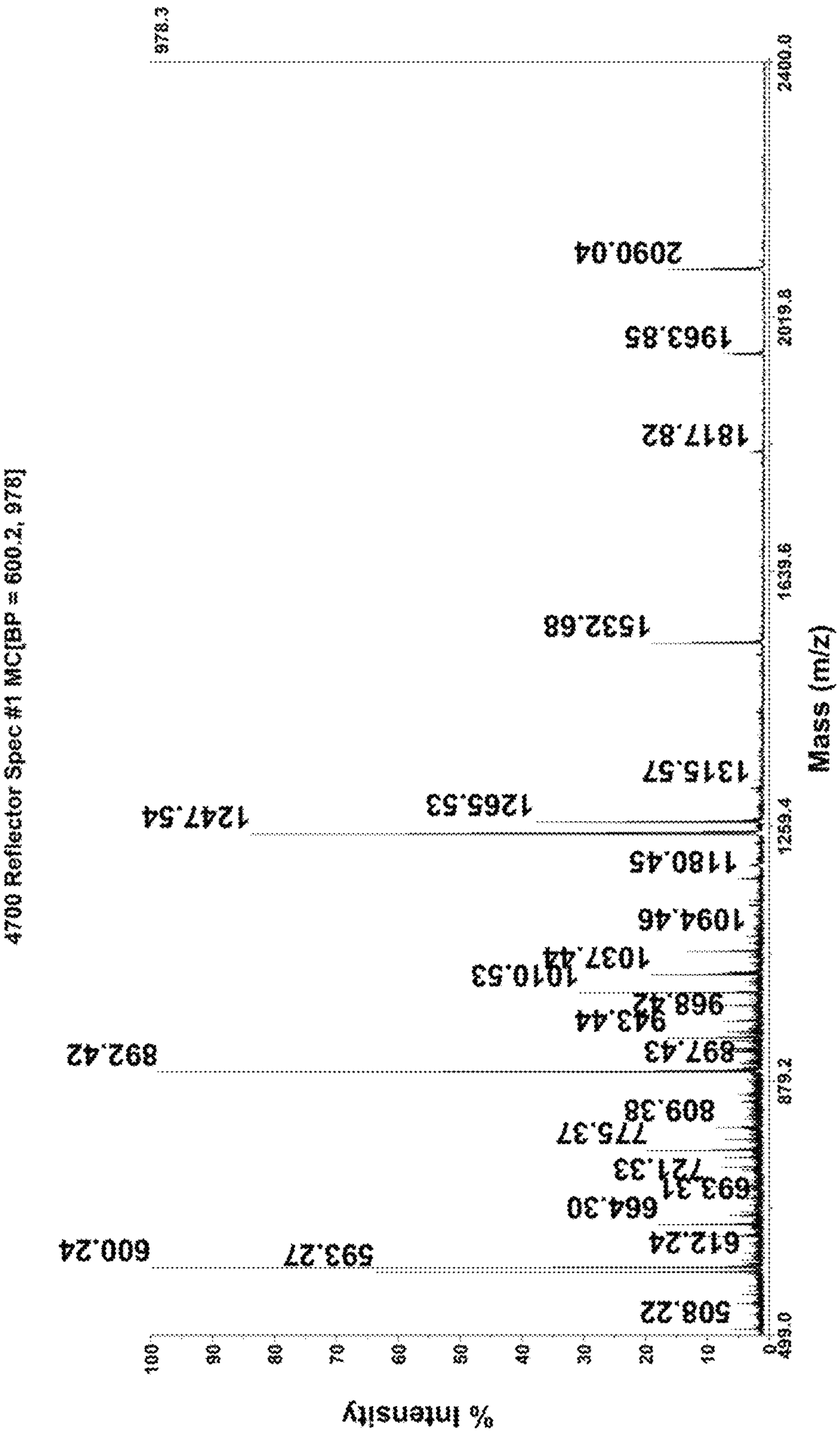
FIG. 7 is a one-dimensional mass spectrogram of component G5-2 according to some embodiments of the present disclosure.
Figure 8:
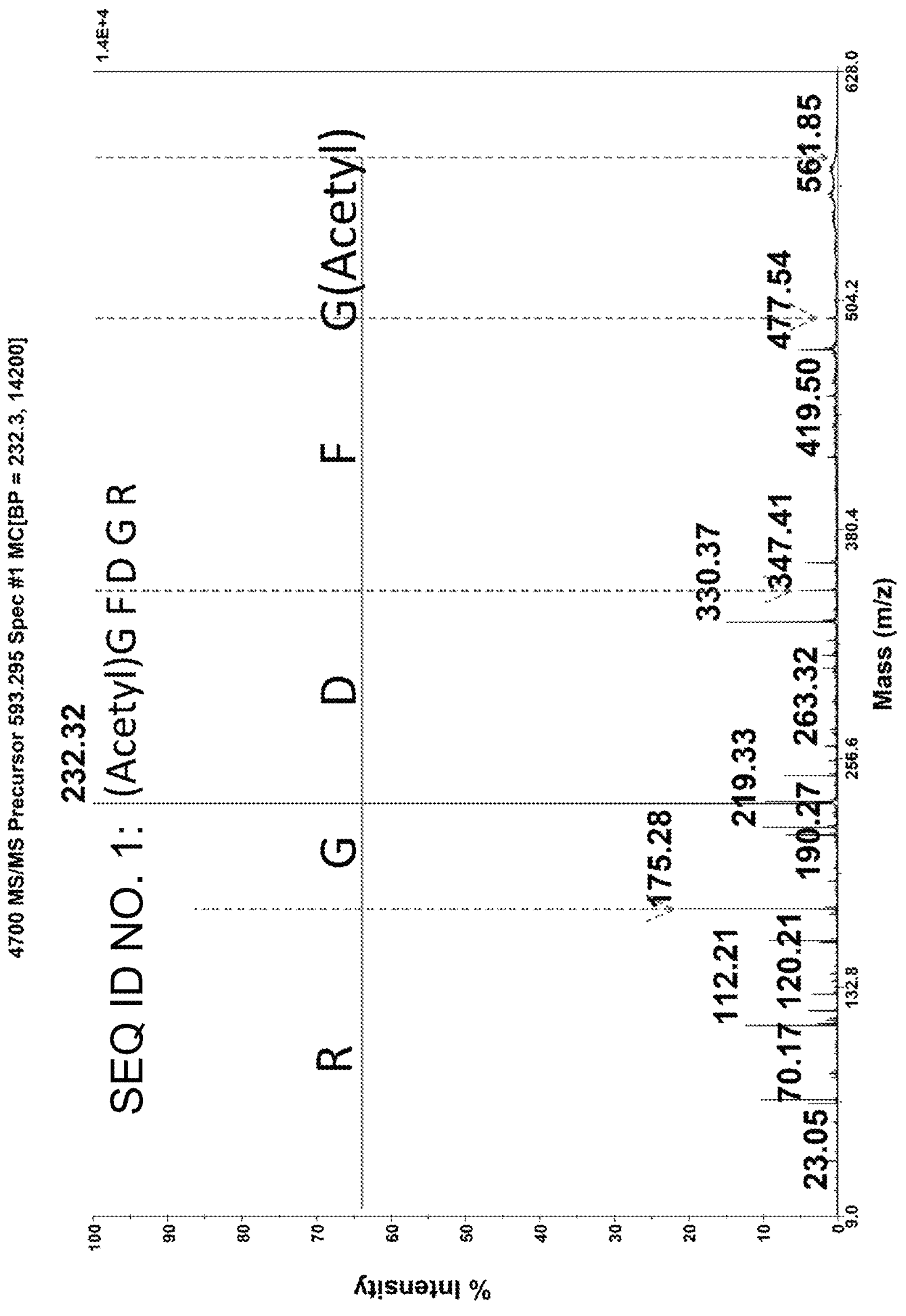
FIG. 8 is a two-dimensional mass spectrogram of component G5-2-1 (SEQ ID NO. 1) according to some embodiments of the present disclosure.
Figure 9:
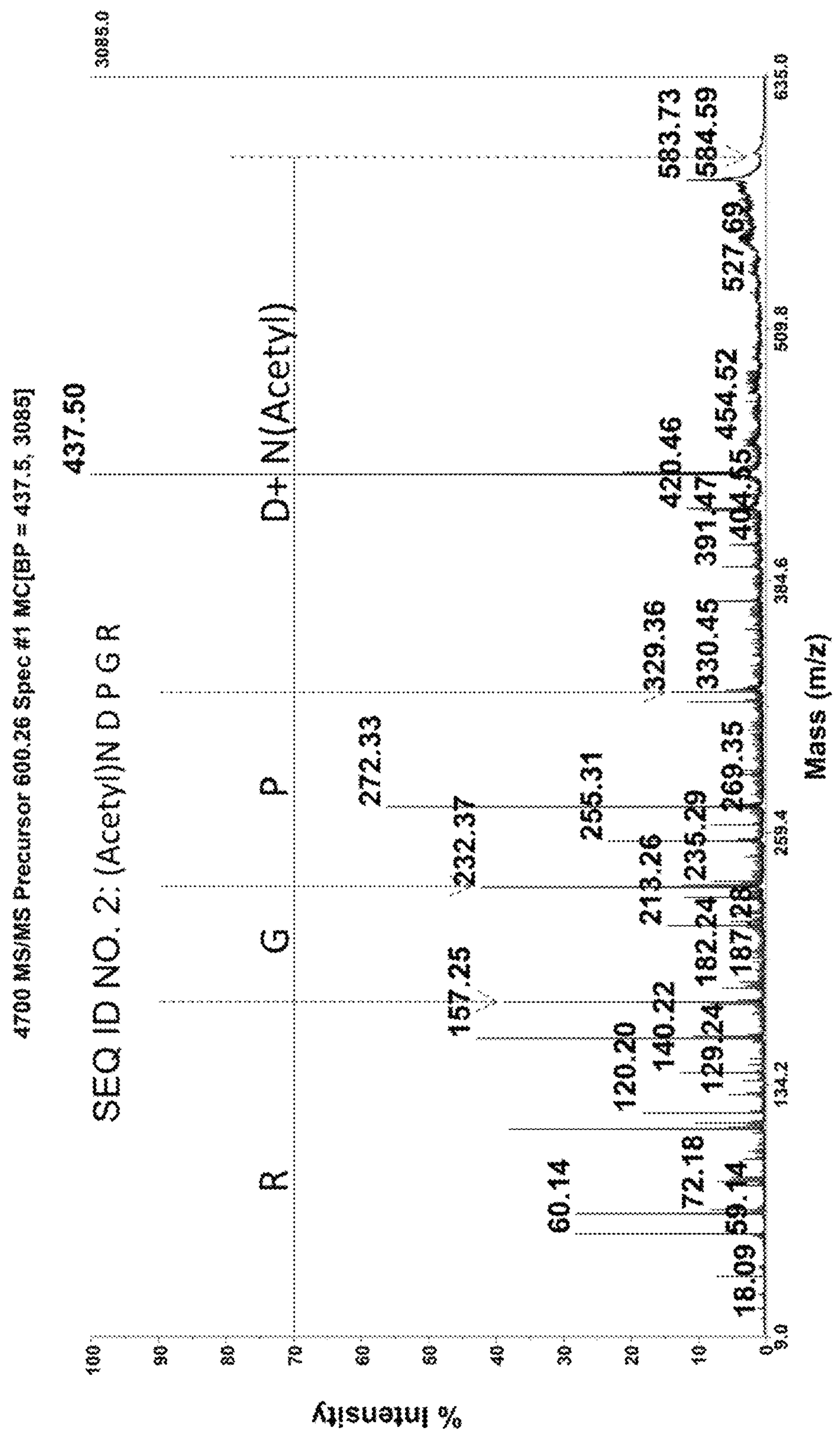
FIG. 9 is a two-dimensional mass spectrogram of component G5-2-2 (SEQ ID NO. 2) according to some embodiments of the present disclosure.
Figure 10:
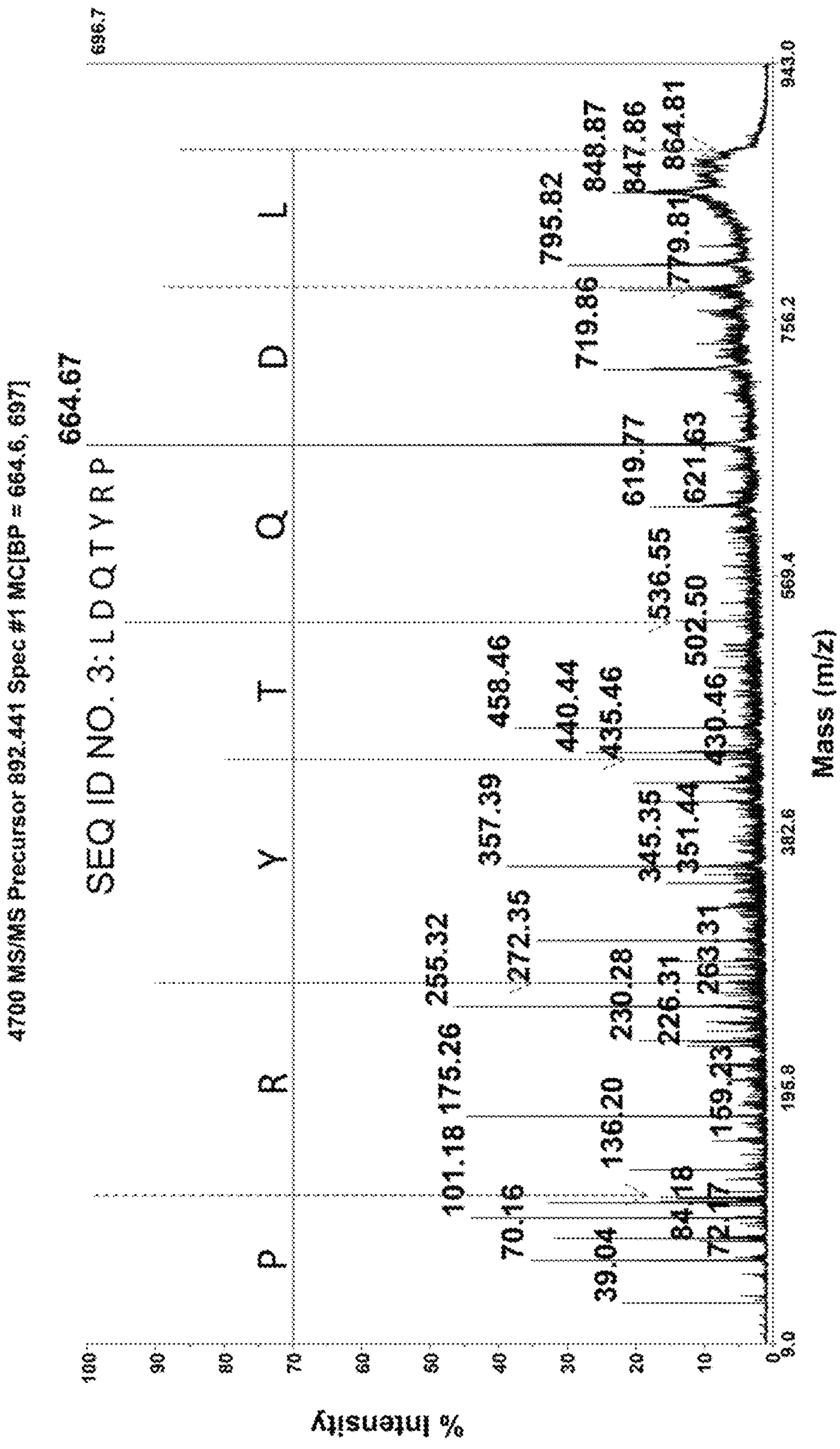
FIG. 10 is a two-dimensional mass spectrogram of component G5-2-3 (SEQ ID NO. 3) according to some embodiments of the present disclosure.
Figure 11:
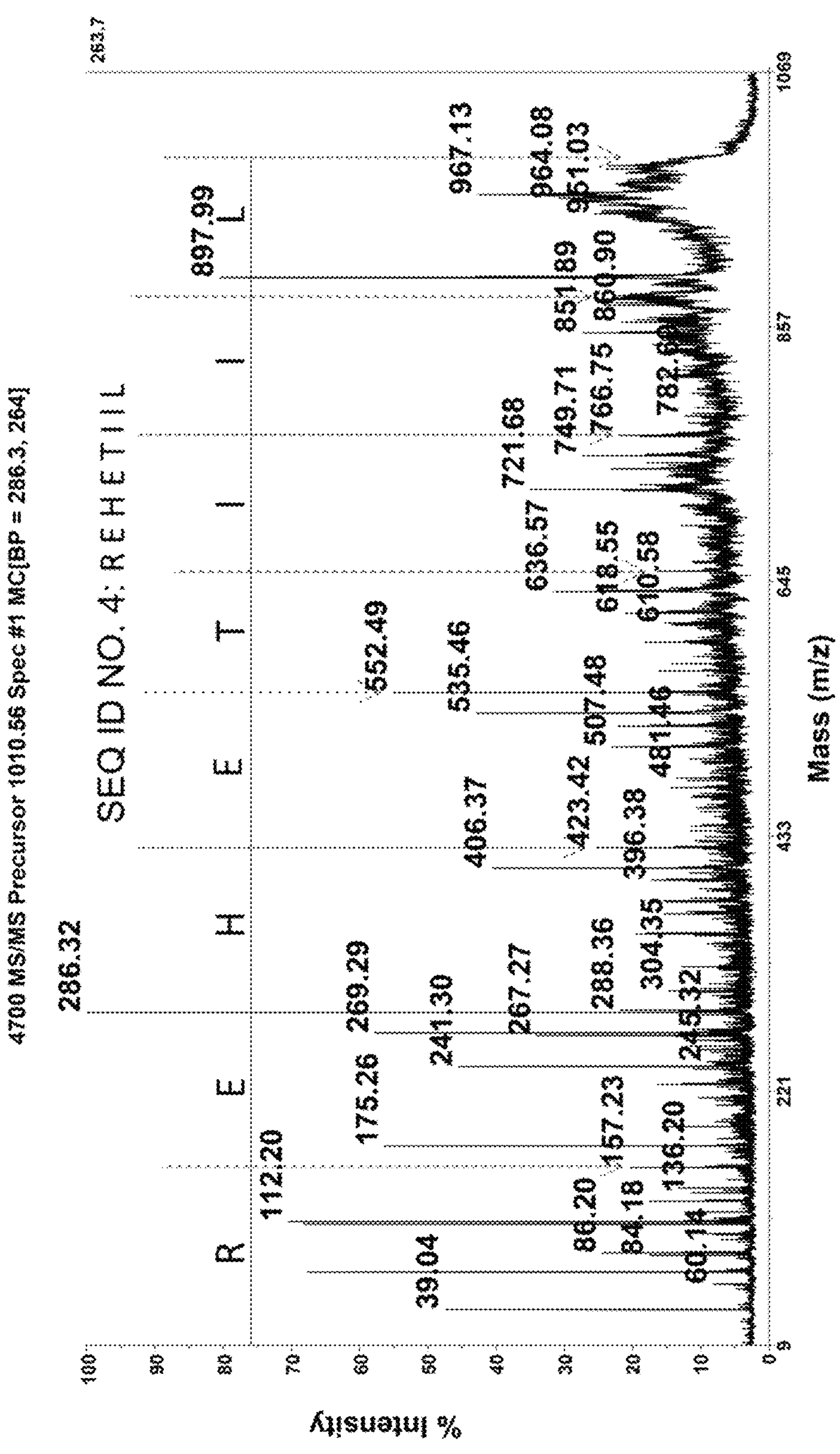
FIG. 11 is a two-dimensional mass spectrogram of component G5-2-4 (SEQ ID NO. 4) according to some embodiments of the present disclosure.
Figure 12:
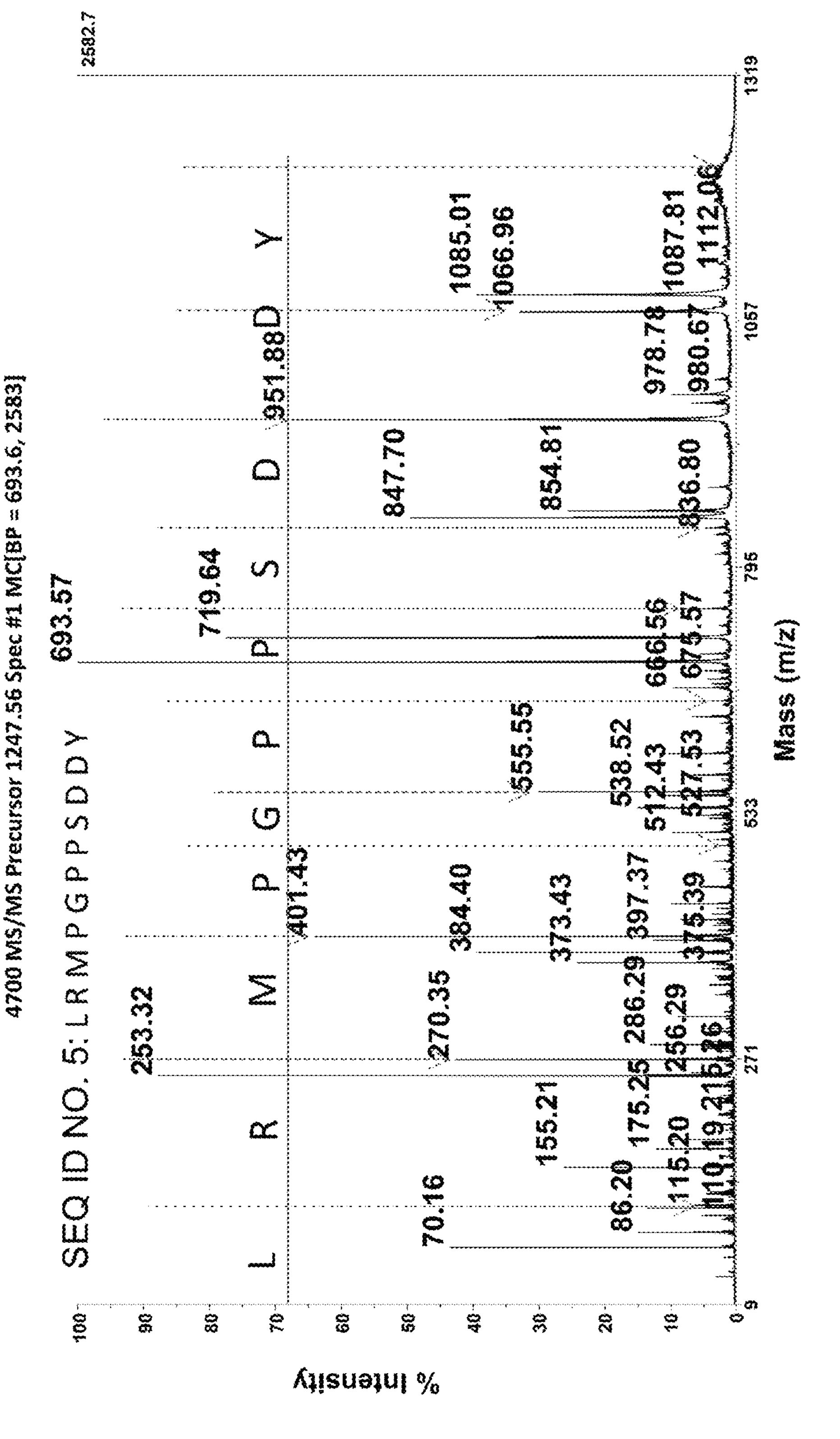
FIG. 12 is a two-dimensional mass spectrogram of component G5-2-5 (SEQ ID NO. 5) according to some embodiments of the present disclosure.
Figure 13:
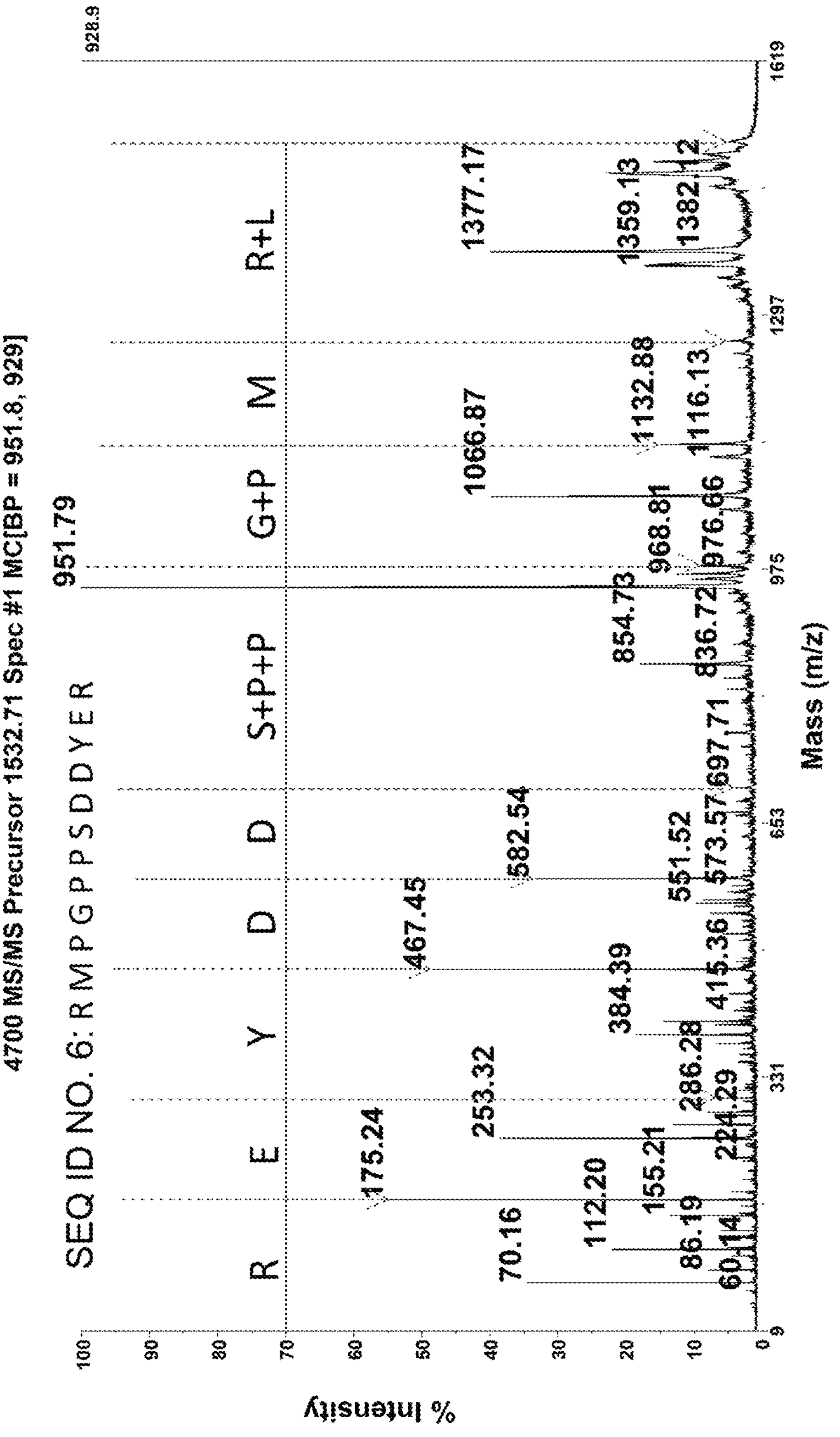
FIG. 13 is a two-dimensional mass spectrogram of component G5-2-6 (SEQ ID NO. 6) according to some embodiments of the present disclosure.

The high purity G5-2 is analyzed by mass spectrometry with 4700 series time-of-flight mass spectrometer, and the results of one-dimensional mass spectrometry are shown in FIG. 7.

The result of mass spectrometry in FIG. 7 shows that component G5-2 mainly contains six major absorption peaks with molecular weights of 593.30 Da, 600.24 Da, 892.42 Da, 1010.53 Da, 1247.54 Da and 1532.68 Da, which are respectively identified as component G5-2-1, component G5-2-2, component G5-2-3, component G5-2-4, component G5-2-5 and component G5-2-6, indicating that component G5-2 is not composed of a single component, but mainly contains 6-10 kinds of small peptides, and that the effective component of ACE inhibitory peptide composition is small peptides less than 2000 Da.

B. Secondary Mass Spectrometry

Components G5-2-1, G5-2-2, G5-2-3, G5-2-4, G5-2-5 and G5-2-6 are determined and analyzed by MS/MS mass spectrometry, and the results are shown in FIGS. 8, 9, 10, 11, 12 and 13 respectively.

The analysis tool of instrument software 4700 Explorer is adopted, and sequencing is carried out by De Novo Explorer. The experimental results of sequencing are shown in Table 1.

TABLE 1

Amino acid sequence of ACE inhibitory peptide composition derived from ginkgo protein

| Components | Amino acid sequence |
|---|---|
| G5-2-1 | GFDGR (SEQ ID NO: 1) |
| G5-2-2 | NDPGR (SEQ ID NO: 2) |
| G5-2-3 | LDQTYRP (SEQ ID NO: 3) |
| G5-2-4 | REHETIIL (SEQ ID NO: 4) |
| G5-2-5 | LRMPGPPSDDY (SEQ ID NO: 5) |
| G5-2-6 | LRMPGPPSDDYER (SEQ ID NO: 6) |

From the sequencing results in Table 1, it can be seen that the functional components in component G5-2 are mainly composed of two pentapeptides, one heptapeptide, one octapeptide, one dodecapeptide and one tridecapeptide, and their amino acid sequences are shown in SEQ ID NO: 1-SEQ ID NO: 6 respectively. Therefore, the ACE inhibitory peptide composition derived from ginkgo protein includes the amino acid sequences shown in SEQ ID NO: 1-SEQ ID NO: 6.

TEST EXAMPLE 1

Screening of Enzymes for Hydrolysis

Under the conditions of 7% of ginkgo protein concentration and 5% of E/S (mass concentration ratio of enzyme to substrate), the ginkgo protein is hydrolyzed for 6 h under the conditions of optimum temperature and optimum reaction pH of the four proteases in table 2. After hydrolysis, the enzyme is inactivated by keeping it in a boiling water bath at 100° C. for 15 min and then centrifuged at 4000 r/min for 30 min, and the supernatant is freeze-dried. After drying, the ACE inhibitory activities of the hydrolysates of four proteases are determined. ACE inhibitory activity is determined by high performance liquid chromatography. The specific determination method is as follows.

20 L of inhibitor (the above protease hydrolysate) is added into 120 μL of HHL substrate solution with a concentration of 5 mM and mixed uniformly, 10 μL of ACE (1 mU) is added and mixed uniformly, reacting at 37±1° C. for 60 min, and then 150 L of 1 mol/L of HCl is added to stop the reaction to obtain the sample solution. The sample solution is filtered with 0.45 μm filter membrane, and ACE inhibitory activity is determined by HPLC system. 20 L of 0.05 mol/L of boric acid buffer with pH 8.3 is used as the control group instead of inhibitor. ACE inhibitory activity is calculated according to the following formula (1):

$$ACE\ \text{inhibitory activity}\ \% = \frac{P-Q}{P} \times 100\%, \quad (1)$$

where P is the peak area of hippuric acid in the control group (mAU·s); Q is the peak area of hippuric acid in the inhibitor group (mAU·s).

The detection and analysis conditions of HPLC are as follows:

| Chromatographic column: SinoChrom ODS-BP C18 column (4.6 mm i.d. × 250 mm, Particle size of filler is 5 μm) | |
|---|---|
| Detection wavelength: 228 nm | Flow rate: ImL/min |
| The mobile phase A: water (containing 0.05% of TFA) | Mobile phase B: acetonitrile (containing 0.05% of TFA) |
| Injection volume: 50 μL, automatic injection | Column temperature: 30° C. |
| Gradient elution condition: 20-70% B(10 min); 70-0% B (2 min) | |

The test results are shown in Table 2.

TABLE 2

Comparison of ACE inhibitory activities of four protease hydrolysates ($\overline{X}$ ± SE)

| Types of proteases | Inhibitory activity of hydrolysate (%) |
|---|---|
| AS1.398 neutral protease | $87.36 \pm 3.19^a$ |
| Trypsin | $61.34 \pm 1.79^b$ |
| Caroid | $73.15 \pm 2.65^c$ |
| Alcalase | $80.43 \pm 1.52^d$ |

Note:
Duncan,
$^a$= 0.01; in the same column of data, the same letter means no significant difference, while the different letter means significant difference.

The ACE inhibitory activities of hydrolysates in Table 2 are compared by Duncan's new repolarization method, and it is found that the ACE inhibitory activities of AS1.398 neutral protease hydrolysate, trypsin hydrolysate, papain hydrolysate and Alcalase hydrolysate are significantly different (P<0.01). The order of the ACE inhibitory activity of the four protease hydrolysates is: AS1.398 neutral protease>Alcalase>papain>trypsin. Among them, the ACE inhibitory activity of neutral protease hydrolysate AS1.398 is the highest, which is about 87%. Therefore, when ACE inhibitory activity is taken as an index for preparing ACE inhibitory peptide derived from ginkgo protein by selected hydrolysis enzyme, AS1.398 neutral protease can be selected as hydrolysis enzyme. In addition, AS1.398 neutral protease produced by *Bacillus subtilis* fermentation has the advantages of stable source, low production cost and the like, and the neutral protease has mild reaction conditions and is suitable for the requirements of industrial production, and is an ideal enzyme for industrial use. Therefore, AS1.398 neutral protease (purchased from Wuxi Enzyme Preparation Factory, Jiangsu Province) is selected as the test enzyme in the preparation method in Embodiment 1. It should be noted that Alcalase and papain can also be used as hydrolysis enzymes for preparing ACE inhibitory peptides from ginkgo proteins.

TEST EXAMPLE 2

Optimization of Hydrolysis Conditions of AS1.398 Neutral Protease

As1.398 neutral protease is used as the experimental enzyme to optimize the optimum hydrolysis conditions. Under the conditions of hydrolysis time of 6 h and enzyme dosage (E/S) of 5%, the extraction temperature (A), pH(B) and substrate concentration (C) are selected as the test factors, and the inhibitory activity of ACE is taken as the detection index, and the response surface design is adopted to optimize the hydrolysis process conditions. See Table 3 for the factor level table.

TABLE 3

Level Table of Combined Test Factors of Process Optimization Center

| Test number | Level −1 | Level 0 | Level 1 |
|---|---|---|---|
| A Extraction temperature/° C. | 40 | 45 | 50 |
| B pH | 6.0 | 7.0 | 8.0 |
| C Substrate concentration/% | 4.0 | 7.0 | 10.0 |

AS1.398 neutral protease is used as the test enzyme, the central composite design of response surface is adopted to screen the best hydrolysis conditions, and the test results are shown in Table 4.

TABLE 4

Test results of optimization center combination for hydrolysis process of AS1.398 neutral protease

| Test No. | A Extraction temperature (° C.) | B pH | C Substrate concentration (%) | ACE inhibition rate/% |
|---|---|---|---|---|
| 1 | 1 | −1 | 0 | 70.85 |
| 2 | −1 | 0 | −1 | 70.23 |
| 3 | 0 | 1 | −1 | 84.21 |
| 4 | 0 | 0 | 0 | 89.95 |
| 5 | -1 | 0 | 1 | 75.00 |
| 6 | 0 | 0 | 0 | 89.89 |
| 7 | 0 | 1 | 1 | 85.12 |
| 8 | 1 | 0 | −1 | 78.23 |
| 9 | 0 | 0 | 0 | 89.35 |
| 10 | 0 | −1 | −1 | 75.69 |
| 11 | 0 | 0 | 0 | 89.71 |
| 12 | 0 | −1 | 1 | 77.14 |
| 13 | −1 | −1 | 0 | 68.63 |
| 14 | 0 | 0 | 0 | 89.15 |
| 15 | 1 | 0 | 1 | 76.48 |
| 16 | −1 | 1 | 0 | 73.82 |
| 17 | 1 | 1 | 0 | 80.58 |

Using Design-Expert 7.1 software, the response value (ACE inhibitory activity) in Table 4 and various factors are regressed and fitted to obtain a regression equation, and the results of the regression equation are analyzed. The regression analysis results are shown in Table 5.

The regression equation is:

$$Y=89.61+2.31A+3.93B+0.67C+1.13AB—1.63AC—0.13BC—10.85A2—5.29B2—3.78C2;$$

TABLE 5

Regression analysis results

| Variance source | Sum of squares | Freedom | Mean square | F value | P value | Significance |
|---|---|---|---|---|---|---|
| A | 42.60 | 1 | 42.60 | 338.47 | <0.0001 | *** |
| B | 123.40 | 1 | 123.40 | 980.55 | <0.0001 | *** |
| C | 3.62 | 1 | 3.62 | 28.75 | 0.0011 | ** |
| AB | 5.15 | 1 | 5.15 | 40.94 | 0.0004 | *** |
| AC | 10.63 | 1 | 10.63 | 84.45 | <0.0001 | *** |
| BC | 0.073 | 1 | 0.073 | 0.58 | 0.4715 | |
| $A^2$ | 495.45 | 1 | 495.45 | 3936.79 | <0.0001 | *** |
| $B^2$ | 117.94 | 1 | 117.94 | 937.14 | <0.0001 | *** |
| $C^2$ | 60.08 | 1 | 60.08 | 477.41 | <0.0001 | *** |
| Model | 918.61 | 9 | 102.07 | 811.02 | <0.0001 | |
| Residual | 0.88 | 7 | 0.13 | | | |
| Mismatched term | 0.40 | 3 | 0.13 | 1.10 | 0.4470 | |
| Pure error | 0.48 | 4 | 0.12 | | | |
| Overall error | 919.49 | 16 | | | | |

Note:

*. P < 0.05, the difference is significant;

**. P < 0.01, the difference is highly significant;

***. P < 0.001, the difference is extremely significant.

According to the analysis results in table 5, the F of the model is F=811.02, P<0.0001, which indicates that the quadratic model used in the experiment is extremely significant and of statistical significance. The missing term is used to indicate the degree of fitting between the model and the experiment, that is, the degree of difference between the two. The experiment P=0.4470>0.05 is beneficial to the model, and there is no mismatching factor. Therefore, the regression equation can be used to analyze the experimental results instead of the actual points.

The extraction temperature of factor A and factor B with the pH of $P<0.0001$, which indicates that factors A and B have significant effects on ACE inhibition rate; The factor C substrate concentration $P=0.0011<0.01$, indicating that factor C has a highly significant effect on ACE inhibition rate. However, the P values of A2, B2 and C2 are all less than 0.001, which indicates that A2, B2 and C2 have a very significant effect on ACE inhibition rate.

P values of interaction items AB and AC are all less than 0.001, so interaction items AB and AC have extremely significant influence on ACE inhibition rate. $P=0.4715$ of interaction term BC is greater than 0.015, so interaction term BC has no effect on ACE inhibition rate.

According to the above analysis, the optimum hydrolysis conditions are as follows: extraction temperature is 45.61° C., pH is 7.38, substrate concentration is 7.17%, and ACE inhibition rate is 90.52%.

Using the optimized hydrolysis conditions mentioned above, experiments are carried out to verify the results determined by the central composite test of response surface. According to the experiment, the ACE inhibition rate is 91.15%, which indicates that the optimal hydrolysis conditions determined by the central composite test of response surface are reliable.

It should be noted that the above method only determines the optimum hydrolysis process conditions, and may also include other hydrolysis process conditions. For example, the extraction temperature may range from 40° C. to 50° C. (for example, 42° C., 43° C., 44° C., 45° C., 45.6° C., 46° C., 47° C., etc.); the pH may be any pH value between 6.5 and 8.5 (for example, 6.8, 7.0, 7.2, 7.3, 7.4, 7.5, 7.8, 8.0, 8.3, etc.); the substrate concentration may be any value between 6.5% and 7.5% (for example, 6.6%, 6.8%, 7%, 7.2%, etc.).

TEST EXAMPLE 3

Optimization of Hydrolysis Time

Under the hydrolysis conditions of AS1.398 neutral protease, that is, ginkgo protein concentration is 7%, E/S (ratio of enzyme to substrate mass concentration) is 5%, and pH is 7.0; the samples are taken at 1 h,3 h,6 h, 9 h,12 h and 24 h respectively, then the enzyme is inactivated, centrifuged, and the supernatant is freeze-dried. After drying, the ACE inhibitory activity of the hydrolysate under different hydrolysis time conditions is determined. The test results are shown in FIG. 14.

Figure 14:
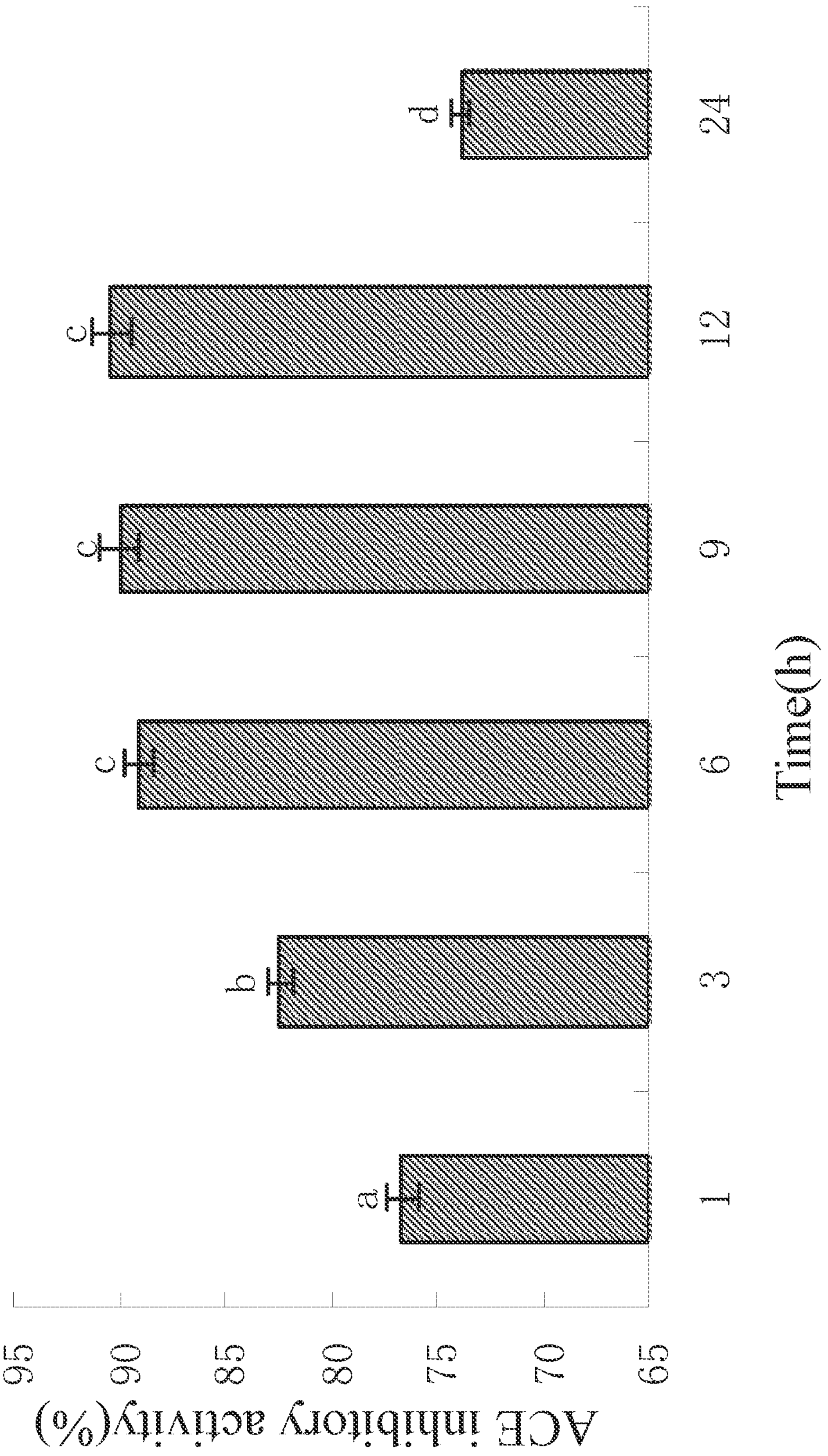
FIG. 14 is a graph showing the relationship between ACE inhibitory activity derived from ginkgo protein and hydrolysis time of hydrolysate under different hydrolysis time according to some embodiments of the present disclosure.

According to the multiple comparison results in FIG. 14, the ACE inhibitory activities of hydrolysates with hydrolysis time of 1 h, 3 h, 6 h and 24 h are significantly different ($P<0.05$), while the ACE inhibitory activities of hydrolysates with hydrolysis time of 6 h, 9 h and 12 h are not significantly different ($P>0.05$). In the process of hydrolysis, the hydrolysis time is within 1 h, and the hydrolysate obtains high ACE inhibitory activity, which is 76.71%. With the further extension of hydrolysis time, the ACE inhibitory activity of hydrolysate increases. When the hydrolysis time is 12 h, the inhibitory activity of ACE reaches the maximum (90.45%), and then the inhibitory activity of ACE decreases slowly. When the hydrolysis time is 24 h, the ACE inhibitory activity of the hydrolysate reduces to 73.86%. From the above results, it can be seen that the ACE inhibitory activity of hydrolysate will decrease if the hydrolysis time is too long. Therefore, the hydrolysis time of AS1.398 neutral protease is selected as 6h to prepare ACE inhibitory peptide composition derived from ginkgo protein. In some embodiments, the hydrolysis time can also be any time period in 5-14 h, for example, 8 h, 9 h, 10 h, 12 h, etc.

TEST EXAMPLE 4

Effect of Ultrafiltration Separation on ACE Inhibitory Activity of Enzymatic Hydrolysate After ultrafiltration separation with different molecular weight cut-off, 3 kDa ultrafiltration component, 3-10 kDa ultrafiltration component and over 10 kDa ultrafiltration component are collected, and their ACE inhibitory activities are determined. The test results are shown in Table 5.

TABLE 5

Effect of ultrafiltration on ACE inhibitory activity of enzymatic hydrolysate

| Type | ACE inhibitory activity (%) |
|---|---|
| Enzymatic hydrolysate | 64.18 ± 0.97[a] |
| Over 10 kDa concentrated solution | 56.23 ± 1.45[b] |
| Ultrafiltrate of 3-10 kDa | 71.97 ± 0.91[c] |
| Ultrafiltrate below 3 kDa | 85.34 ± 1.62[d] |

Note:

Duncan,

[a]= 0.01; in the same column of data, the same letter means no significant difference, while the different letter means significant difference.

From the analysis results in Table 5, it can be seen that the ACE inhibitory activity of ultrafiltrate with different molecular weight cut-off is significantly different ($P<0.01$) after the ginkgo proteolysis product is separated by ultrafiltration. The ACE inhibitory activity derived from ginkgo protein hydrolysate is improved after being extracted and separated by 10 kDa and 3 kDa ultrafiltration membranes. Compared with ginkgo protein hydrolysate, the ACE inhibitory activity of 3-10 kDa ultrafiltration component and 3 kDa ultrafiltration component is significantly improved ($P<0.01$). The ACE inhibitory activity of 3-10 kDa ultrafiltration component is 1.12 times that of ginkgo protein hydrolysate. The ACE inhibitory activity of 3 kDa ultrafiltration component is 1.32 times that of ginkgo protein hydrolysate. The ACE inhibitory activity of ultrafiltration concentrate components above 10 kDa is 7.95% lower than that of ginkgo protein hydrolysate. Therefore, ultrafiltration can effectively separate the ACE inhibitory peptide composition derived from ginkgo protein and improve the ACE inhibitory activity of the hydrolysate. In some embodiments, the molecular weight of ultrafiltration interception may be below 10 kDa, below 5 kDa, below 3 kDa, etc.

The above embodiments only describe the preferred mode of the present disclosure, but do not limit the scope of the present disclosure. On the premise of not departing from the design spirit of the present disclosure, various modifications and improvements made by those of ordinary skill in the art to the technical scheme of the present disclosure shall fall within the protection scope defined by the claims of the present disclosure.

What is claimed is:

1. A preparation method of an ACE inhibitory peptide composition consisting of six small purified peptides with amino acid sequences of GFDGR (SEQ ID NO. 1), NDPGR (SEQ ID NO. 2), LDQTYRP (SEQ ID NO. 3), REHETIIL (SEQ ID NO. 4), LRMPGPPSDDY (SEQ ID NO. 5) and LRMPGPPSDDYER (SEQ ID NO. 6), comprising the following steps:

(1) preparing defatted ginkgo nut powder by defatting ginkgo nut powder with petroleum ether to obtain the defatted ginkgo nut powder;

(2) preparing ginkgo protein by:

firstly, after mixing the defatted ginkgo nut powder obtained in step (1) with water, adding NaOH solution to adjust its pH to 10.0, then, extracting at 40-45° C., and subsequently, after centrifugation the extract to obtain supernatant, adjusting pH of the supernatant to 4-4.5 with HCl solution, and centrifuging the supernatant after pH adjustment to obtain ginkgo protein powder;

(3) hydrolyzing ginkgo protein by:

firstly, preparing the ginkgo protein powder obtained in step (2) into a protein solution with a substrate concentration of 7.17%, then, adding NaOH solution into the protein solution to adjust the pH to 7.40, and adding 5% of AS1.398 neutral protease for hydrolysis when the temperature of the reaction reaches 45.6° C.; and after hydrolysis for 6 h, collecting supernatant after centrifugation to obtain ginkgo protein hydrolysate;

(4) separating ginkgo protein hydrolysate by:

ultrafiltering and separating the ginkgo protein hydrolysate obtained in step (3) by an ultrafiltration membrane with a molecular weight cut-off of 3 kDa to obtain ultrafiltration permeate;

(5) preparing crude ACE inhibitory peptide derived from ginkgo protein by:

freeze-drying the ultrafiltration permeate obtained in step (4) to obtain crude ACE inhibitory peptide derived from ginkgo protein; and (6) preparing ACE inhibitory peptide composition derived from ginkgo protein by:

separating and purifying the crude ACE inhibitory peptide derived from ginkgo protein obtained in step (5) by a reversed-phase chromatographic column, eluting and separating components at the wavelength of 220 nm, and collecting a first component with the strongest ACE inhibitory activity, separating and purifying the first component with the strongest ACE inhibitory activity at the wavelength of 220 nm by using a peptide chromatographic column, and collecting a second component with the strongest ACE inhibitory activity, and purifying the second component with the strongest ACE inhibitory activity by using a peptide chromatographic column to obtain the ACE inhibitory peptide composition derived from ginkgo protein.

2. The preparation method according to claim 1, wherein the mass-volume ratio of the ginkgo nut powder and the petroleum ether in step (1) is 1:12.

3. The preparation method according to claim 1, wherein the concentration of the NaOH solution in step (2) is 6 mol/L, and the concentration of the HCl solution is 6 mol/L.

4. The preparation method according to claim 1, wherein the centrifugation condition is 4000 r/min for 30 min.

* * * * *

SEQUENCE LISTING

```
Sequence total quantity: 6
SEQ ID NO: 1            moltype = AA  length = 15
FEATURE                 Location/Qualifiers
source                  1..15
                        mol_type = protein
                        organism = synthetic construct
SEQUENCE: 1
GLYPHEASPG LYARG                                                 15

SEQ ID NO: 2            moltype = AA  length = 15
FEATURE                 Location/Qualifiers
source                  1..15
                        mol_type = protein
                        organism = synthetic construct
SEQUENCE: 2
ASNASPPROG LYARG                                                 15

SEQ ID NO: 3            moltype = AA  length = 21
FEATURE                 Location/Qualifiers
source                  1..21
                        mol_type = protein
                        organism = synthetic construct
SEQUENCE: 3
LEUASPGLNT HRTYRARGPR O                                          21

SEQ ID NO: 4            moltype = AA  length = 24
FEATURE                 Location/Qualifiers
source                  1..24
                        mol_type = protein
                        organism = synthetic construct
SEQUENCE: 4
ARGGLUHISG LUTHRILEIL ELEU                                       24

SEQ ID NO: 5            moltype = AA  length = 33
FEATURE                 Location/Qualifiers
source                  1..33
                        mol_type = protein
                        organism = synthetic construct
SEQUENCE: 5
LEUARGMETP ROGLYPROPR OSERASPASP TYR                             33

SEQ ID NO: 6            moltype = AA  length = 39
FEATURE                 Location/Qualifiers
source                  1..39
                        mol_type = protein
                        organism = synthetic construct
SEQUENCE: 6
LEUARGMETP ROGLYPROPR OSERASPASP TYRGLUARG                       39
```